(12) United States Patent
Horvath et al.

(10) Patent No.: US 11,571,335 B2
(45) Date of Patent: Feb. 7, 2023

(54) LASER SYSTEM FOR EYE SURGERY

(71) Applicant: Lensar, Inc., Orlando, FL (US)

(72) Inventors: Christopher Horvath, Mission Viejo, CA (US); Vanessa Isabella Vera, Mission Viejo, CA (US)

(73) Assignee: Lensar, Inc., Orlando, FL (US)

( * ) Notice: Subject to any disclaimer, the term of this patent is extended or adjusted under 35 U.S.C. 154(b) by 0 days.

(21) Appl. No.: 14/842,747

(22) Filed: Sep. 1, 2015

(65) Prior Publication Data

US 2016/0089269 A1 Mar. 31, 2016

Related U.S. Application Data

(62) Division of application No. 13/492,788, filed on Jun. 8, 2012, now Pat. No. 9,259,354.

(60) Provisional application No. 61/619,386, filed on Apr. 2, 2012.

(51) Int. Cl.
*A61F 9/007* (2006.01)
*A61F 9/008* (2006.01)
*A61B 18/20* (2006.01)

(52) U.S. Cl.
CPC ...... *A61F 9/00745* (2013.01); *A61F 9/00821* (2013.01); *A61F 9/00825* (2013.01); *A61B 18/20* (2013.01); *A61F 9/008* (2013.01); *A61F 9/00804* (2013.01); *A61F 2009/0087* (2013.01); *A61F 2009/00872* (2013.01); *A61F 2009/00887* (2013.01); *A61F 2009/00889* (2013.01); *A61F 2009/00897* (2013.01)

(58) Field of Classification Search
CPC ............ A61F 9/008; A61F 2009/00872; A61F 9/00821; A61F 9/00804; A61F 2009/00887; A61F 2009/0087; A61F 9/00745; A61F 9/00825; A61F 2009/00897; A61F 2009/00889; A61B 18/20; A61B 90/50
USPC ............................................... 606/4, 5, 6, 10
See application file for complete search history.

(56) References Cited

U.S. PATENT DOCUMENTS

| 4,729,373 A | 3/1988 | Peyman |
| 4,825,865 A | 5/1989 | Zelman |
| 4,946,452 A | 8/1990 | Py |
| 5,057,098 A | 10/1991 | Zelman |

(Continued)

FOREIGN PATENT DOCUMENTS

| EP | 2057973 | 5/2009 |
| JP | 2015 02964 | 2/2015 |

(Continued)

OTHER PUBLICATIONS

Jul. 7, 2021, WIPO, 2021/0259880—Opinin and search report.

(Continued)

*Primary Examiner* — Gary Jackson
*Assistant Examiner* — Sebastian X Lukjan
(74) *Attorney, Agent, or Firm* — Glen P. Belvis; Belvis Law, LLC.

(57) ABSTRACT

The here described invention generally relates to systems for laser eye surgery. It certain embodiments it discloses systems to perform femtosecond eye surgery without docking between the laser delivery system and the patient's eye as well as certain laser delivery system configurations that allow integration of laser delivery systems into a surgical microscope in specific ways, as well as integration into a slit lamp system.

1 Claim, 27 Drawing Sheets

(56) References Cited

U.S. PATENT DOCUMENTS

| | | | |
|---|---|---|---|
| 5,098,426 A | 3/1992 | Sklar | |
| 5,139,504 A | 8/1992 | Zelman | |
| 5,423,801 A | 6/1995 | Marshall | |
| 5,548,352 A | 8/1996 | Dewey | |
| 5,591,160 A | 1/1997 | Reynard | |
| 5,651,783 A | 7/1997 | Reynard | |
| 5,695,461 A | 12/1997 | Schaible | |
| 5,722,970 A | 3/1998 | Colvard et al. | |
| 5,741,244 A | 4/1998 | Klaas | |
| 6,045,527 A | 4/2000 | Appelbaum | |
| 6,391,020 B1 | 5/2002 | Kurtz | |
| 6,494,878 B1* | 12/2002 | Pawlowski | A61F 9/008 606/4 |
| 6,544,254 B1 | 4/2003 | Bath | |
| 6,733,491 B2 | 5/2004 | Kadziauskas | |
| 6,962,583 B2 | 11/2005 | Kadziauskas | |
| 7,182,759 B2 | 2/2007 | Kadziauskas | |
| 8,986,290 B2 | 3/2015 | Patton | |
| 9,050,171 B2 | 6/2015 | Foster | |
| 9,095,415 B2 | 8/2015 | Blumenkranz et al. | |
| 9,107,732 B2 | 8/2015 | Blumenkranz et al. | |
| 9,259,354 B2 | 2/2016 | Horvath | |
| 9,492,318 B2 | 11/2016 | Rockley et al. | |
| 10,709,610 B2 | 7/2020 | Morley et al. | |
| 2003/0050629 A1 | 3/2003 | Kadziauskas | |
| 2003/0073984 A1 | 4/2003 | Maeda | |
| 2003/0174309 A1* | 9/2003 | Dewey | G01J 1/4257 356/73.1 |
| 2004/0034340 A1 | 2/2004 | Biscup | |
| 2006/0084961 A1* | 4/2006 | Kadziauskas | A61B 17/320068 606/15 |
| 2006/0195076 A1* | 8/2006 | Blumenkranz | A61F 9/00736 606/4 |
| 2007/0027470 A1 | 2/2007 | Dodick | |
| 2007/0237620 A1 | 10/2007 | Muhlhoff | |
| 2008/0004608 A1 | 1/2008 | Dacquay | |
| 2008/0013048 A1* | 1/2008 | Gaida | A61F 9/008 351/205 |
| 2008/0071254 A1 | 3/2008 | Lummis | |
| 2008/0319427 A1* | 12/2008 | Palanker | A61F 9/008 606/4 |
| 2009/0018532 A1* | 1/2009 | Salin | A61F 9/00827 606/5 |
| 2009/0137991 A1 | 5/2009 | Kurtz | |
| 2010/0042081 A1* | 2/2010 | Rathjen | A61F 9/009 606/5 |
| 2010/0094264 A1* | 4/2010 | Rathjen | A61F 9/008 606/4 |
| 2011/0022035 A1 | 1/2011 | Porter | |
| 2011/0137299 A1* | 6/2011 | Donitzky | A61F 9/008 606/4 |
| 2011/0288470 A1 | 11/2011 | Boukhny | |
| 2011/0319873 A1* | 12/2011 | Raksi | A61F 9/009 606/1 |
| 2013/0023864 A1 | 1/2013 | Blumenkranz | |
| 2013/0090636 A1* | 4/2013 | Patton | A61F 9/00745 606/6 |
| 2014/0052113 A1 | 2/2014 | Kuehnert | |
| 2014/0104576 A1 | 4/2014 | Bor et al. | |
| 2014/0107634 A1 | 4/2014 | Volgar | |
| 2014/0364870 A1 | 12/2014 | Alvarez et al. | |
| 2015/0190281 A1 | 6/2015 | Patton | |
| 2016/0045367 A1 | 2/2016 | Horvath | |
| 2016/0089269 A1 | 3/2016 | Horvath | |
| 2017/0000645 A1 | 1/2017 | Summers et al. | |
| 2017/0000647 A1 | 1/2017 | Schuele et al. | |
| 2017/0056245 A1 | 3/2017 | Rockley et al. | |
| 2017/0119249 A1 | 5/2017 | Gunn | |
| 2017/0119578 A1 | 5/2017 | Rockley et al. | |
| 2017/0340483 A1 | 5/2017 | Zeiss | |
| 2017/0290703 A1 | 10/2017 | Teuma et al. | |
| 2018/0028355 A1 | 2/2018 | Raksi | |
| 2018/0085256 A1 | 3/2018 | Gray et al. | |
| 2018/0161051 A1 | 6/2018 | Humayun | |
| 2018/0168859 A1 | 6/2018 | Zeiss | |
| 2018/0185043 A1 | 7/2018 | Humayun | |
| 2018/0206717 A1 | 7/2018 | Zeiss | |
| 2018/0250090 A1 | 9/2018 | Patton | |
| 2019/0083308 A1 | 3/2019 | Rathjen | |
| 2019/0096933 A1 | 3/2019 | Kido et al. | |
| 2019/0365567 A1 | 12/2019 | Zeiss | |
| 2021/0259880 A1 | 8/2021 | Newton et al. | |
| 2021/0259881 A1 | 8/2021 | Gray et al. | |
| 2021/0298955 A1 | 9/2021 | McWhirter et al. | |
| 2021/0378864 A1 | 12/2021 | Teuma et al. | |

FOREIGN PATENT DOCUMENTS

| | | | |
|---|---|---|---|
| WO | WO1992017138 | 10/1992 | |
| WO | WO1997022304 | 6/1997 | |
| WO | WO1998012973 | 4/1998 | |
| WO | WO 1999065405 | 12/1999 | |
| WO | WO2006074469 | 7/2006 | |
| WO | WO2009039315 | 3/2009 | |
| WO | WO2009061758 | 5/2009 | |
| WO | WO-2011147570 A1 * | 12/2011 | A61F 9/00736 |
| WO | WO2012047492 | 4/2012 | |
| WO | WO-2012152496 A1 * | 11/2012 | A61B 18/201 |
| WO | WO 2013057098 | 4/2013 | |
| WO | WO2013126653 | 8/2013 | |
| WO | WO2014201165 | 12/2014 | |

OTHER PUBLICATIONS

Apr. 6, 2021, WIPO, 2021/0259881—Opinin and search report.
May 25, 2021, WIPO, 2021/0298955—Opinin and search report.
Jun. 25, 2021, WIPO, 2021/0378864—Opinin and search report.

\* cited by examiner

LASER SYSTEM FOR EYE SURGERY

CROSS-REFERENCE

The present application is a Divisional of the U.S. non-provisional application Ser. No. 13/492,788.

The present application claims the benefit of priority under 35 U.S.C. § 119(e) of U.S. provisional application No. 61/619,386 filed Apr. 2, 2012, the entire content of which is incorporated herein by reference. The present application also claims the benefit of priority under 35 U.S.C. § 119(e) of U.S. provisional application No. 61/495,370 filed Jun. 9, 2011, the entire content of which is incorporated herein by reference.

BACKGROUND OF THE INVENTION

The present invention generally relates to systems, apparatus, and methods related to eye surgery. More particularly, the present invention relates to systems, apparatus and methods for cataract surgery. Cataract surgery is one of the most common ophthalmic surgical procedures performed. The primary goal of cataract surgery is the removal of the defective lens and replacement with an artificial lens or intraocular lens (IOL) that restores some of the optical properties of the defective lens.

The major steps in cataract surgery consist of making cornea incisions to allow access to the anterior chamber of the eye and to correct for astigmatism (Limbal relaxing incisions, LRIs), cutting and opening the capsule of the lens to gain access to the lens, fragmenting and removing of the lens and in most cases placing an artificial intraocular lens in the eye.

The cornea incisions are typically performed with surgical knives or more recently with lasers.

Cutting of the capsule is most commonly done through skillful mechanical cutting and tearing a circle shaped opening, using hand tools. This procedure is called capsulorhexis.

Traditional methods for performing a capsulorhexis are based on mechanical cut and peeling techniques. Another method referred to as YAG laser anterior capsulotomy delivers individual laser pulses with high energy to the eye to assist with the opening of the capsule. The precision and quality of these methods is limited.

More recently, photodisruptive lasers and methods have been introduced that can perform the capsulotomy/capsulorhexis opening cut with great precision. The inventor's prior patents and patent applications regarding photodisruptive lasers for use in eye surgery include: U.S. Pat. Nos. 6,992,765, 7,371,230, U.S. 61/619, U.S. Ser. No. 12/902, 105, and PCT/US11/54506. Photodisruptive laser pulses in the range of <10000 femtoseconds have been successfully applied to make incisions into various tissues of the eye. The main focus to date has been using a femtosecond laser for various cornea incisions such as LASIK flaps, intrastromal incisions, Limbal Relaxing Incisions, Keratoplasties and cornea entry incisions. In more recent years femtosecond lasers have also been successfully applied to the capsule and the lens of the human eye in femtosecond laser assisted cataract procedures.

The main benefit of these photodisruptive laser pulses lays in the fact that the eye tissues that are treated transmit the wavelengths of the typically chosen lasers, usually in the near infrared or visible range and therefore allow the laser to be focused through the cornea, aqueous humor, lens capsule and lens without much scattering or absorption. The laser pulses are always focused to a very small spot size in the range of a few micrometers, so that a laser induced optical breakdown is achieved in any tissue or liquid (e.g. aqueous humor) that falls within the spot size location.

This optical breakdown (photodisruptive breakdown) creates a micro plasma followed by a small cavitation bubble. This photodisruption of tissue can be used to cut and dissect tissue areas of any size and shapes by scanning a sequence of many such laser pulses over a desired volume in the eye.

Since the tissue layers in the laser path above and below the focus point are below the optical breakdown threshold and since they don't significantly absorb the laser wavelength, they remain unaffected by the laser beam. This principle allows non-invasive photo disruptive eye surgery since no incision from the outside needs to be made.

There is a threshold of a minimum laser fluence (laser peak power divided by focus area) required to achieve the optical breakdown. The laser peak power goes up with higher pulse energy (typically in the µJ range) and shorter pulse duration (typically <600 fs). The laser fluence for any given peak power goes up as the focus area goes down. Achieving a small spot size is therefore critical in achieving a high fluence that exceeds the optical breakdown threshold.

The way of achieving a high enough fluence for breakdown by increasing the laser pulse energy is less desirable since a higher pulse energy comes with a larger cavitation bubble and associated shock wave. The larger the cavitation bubble the less precision is achieved in cutting any features with a sequence of pulses. Furthermore a large shock wave is considered a undesired side effect since it has the potential to damage surrounding tissues.

Priority is therefore given to minimizing the spot size to achieve an above threshold laser fluence while using laser pulses within a low pulse energy range of typically <50 µJ per laser pulse. These principles have been successfully implemented in femtosecond eye laser systems treating the cornea or capsule/lens of an eye. Typical laser beam focusing convergence angles required are numerical apertures of NA >0.15 (full angle Θ>15 deg) and in some optimized cases NA >0.3.

According to:

$$\omega_0 = M^2 \frac{360\lambda}{\pi^2 \Theta} \qquad \text{Formula 1}$$

Θ=full focusing convergence angle in degrees
λ=laser wavelength
$\omega_0$=laser beam focus radius defined by $1/e^2$ cut off
$M^2$=beam quality factor determined by the total aberrations If beam aberrations can be kept to a minimum e g $M^2$<1.3 ($M^2$=1 is the theoretical minimum with no aberration at all) then the above focusing angles of NA>0.15 (Θ>15 deg) and NA>0.30 (Θ>30 deg) the resulting spot size diameters (2 $\omega_0$) will be <8 µm and <4 µm respectively (for a laser wavelength λ=1 µm).

The high numerical aperture and minimization of aberrations is critical in achieving such small spot sizes. The laser delivery systems for such laser parameters face several challenges due to the high numerical aperture required for to achieve a very small spot size. These systems get further complicated by using a laser beam that is scanned through the focusing lens assembly. Maintaining low aberration while scanning a laser beam at an incidence angle other than normal (90 degrees of incidence) through a lens that creates a high numerical aperture focused beam, requires a complex system of multiple lenses in a precise arrangement. Additionally, those methods and systems require a patient interface such as an applanation lens to reference and fixate the eye to the laser system. Placement of this patient interface adds significant complexity to the surgical setup and can cause undesired or harmful high intraocular pressures levels for the duration of the laser procedure. The patient interface is typically provided sterile and is used only once therefore adding significant cost to the overall cataract procedure. Additionally, No current patient interface or laser delivery system that can perform the laser cornea incisions and laser capsulotomy is compatible or has been integrated with a standard surgical microscope. Since the cataract surgery requires a surgical operating microscope to be completed, the patient must be moved and repositioned under a surgical microscope after the current laser assisted parts of the procedure have been completed. This causes a significant time delay and logistical effort.

The delivery system, disclosed herein, avoids such a complex focusing lens setup by implementing a specific laser scanning design that allows the focusing lens to always remain under normal incidence (90 degrees) to the incoming laser beam(s). This dramatically reduces the delivery system size, complexity and induced beam aberrations. Furthermore, several novel delivery system integration designs are disclosed that allow a femtosecond laser treatment with or without a patient interface to be integrated with a standard surgical microscope. This application describes, among others, techniques, methods, apparatus and systems for laser based cornea incisions and capsule perforations (capsulotomy) to create an easier capsulorhexis procedure. Implementation of the described techniques, apparatus and systems include: determining a surgical target region in the cornea and anterior capsule of the eye, and applying laser pulses to photo disrupt a portion of the determined target region to create an opening cut on a cornea or capsule of the lens.

SUMMARY OF THE INVENTION

This application relates to techniques, apparatus and systems for laser eye surgery or laser assisted eye surgery.

This invention describes a specific laser delivery system design that can be used for various surgical procedures in the eye. It also includes novel contact lens (patient interface) designs, that work together with the different delivery system versions here presented. Its preferred embodiment is the delivery of a sequence of ultra short (<50000 femtosecond from now on referred here as fs=femtosecond) laser pulses to achieve an optical breakdown inside the eye tissue at a small spot size (typically <10 micrometer in diameter). The sequence of laser pulses can be used to photo disrupt or cut a specific tissue part inside or on the surface of the eye. This delivery system scans the pulses in varying circular patterns achieving a combination of full and partical circular cut patterns at varying depth of the cut plane. The invention includes specific methods and designs to control and minimize laser beam wavefront abberations, so that a very small focusing spot size can be achieved even without a hard connection between the eye (with or without a contact lens) and the delivery system optics.

A novel aspect of the various embodiments of the invention includes the use of a scanning system, that leaves the focusing lens (assembly) always under a normal (90 degrees) optical incidence angle and therefore dramatically minimizes optical aberrations, that normally require complex optical lens systems to compensate. This design approach allows for the use of a very simple and small main focusing lens (assembly). The various embodiments of the invention allow for no contact between the laser delivery system and the eye.

Some embodiments of the invention comprise a method for forming an incision in eye tissue. The said method comprising: directing a femtosecond laser beam in an axial direction, moving a lens, over a path within the beam, wherein a plane of the lens remains perpendicular to the axial direction and the lens focuses an incident portion of the laser beam to a spot within the eye tissue. The spot has a size which will photo-disrupt tissue along a two dimensional path determined by the path of the lens. Some embodiments further comprise the step of controlling exapansion of the femtosecond laser beam and comprise the apparatus required to adjust beam expansion. Such apparatus or means include beam expanders and Galileo lenses or other means well known in the art.

The above and other embodiments of the invention may further comprise the step of controlling a depth of focus of the laser spot to create a three dimensional treatment area within the eye tissue. One method of controlling the depth of focus of the laser spot applicable to any typical embodiment of the invention comprises the step of moving the focusing lens in its mounting back and forward along the axial direction. Another method of controlling the depth of focus of the laser spot applicable to any typical embodiment of the invention comprises the step of adjusting the collimation angle of the beam after it exits a beam expander and prior to the beam striking the lens. This collimation angle is referred to herein as the exit expansion. The beam expander, described above, may be used to accomplish this task. Adjusting the exit expansion of the beam, as herein described, means increasing or decreasing the divergence of the femtosecond laser beam. Adjusting the expansion exit of the beam may be accomplished by various methods such as controlling the distance between a pair of lenses in a Galileo telescope or adjustment by a beam expander. Typically, the lens is moved over a circular path to create a cylindrical incision in the eye tissue. Other lens path geometries may be used to create various incision patterns in the eye tissue. Additionally, in any aspect of the invention described herein, the lens may be rotated about its own axis in addition to being moved over a path within the beam. Such rotation may be useful when compensating for aberration. Additionally, some embodiments of the invention further include measures to block portions of the femtosecond laser beam which are not incident on the lens.

The invention may be applied to any eye tissue. Typically in the case of performing a capsulorexis or capsulotomy the eye tissue comprises a lens capsule. However, in other uses the eye tissue may include but is not limited to the lens, cornea, vitrious, retina, and anterior chamber.

In preferred embodiments of the invention moving the lens comprises rotating a lens support about an axis parallel to the axial direction of the beam axis, wherein a center of the lens is radially offset from the support axis. The lens support may comprise an opaque material for the purposes of blocking the laser beam. Typically, the lens is an opaque disc which allows the laser beam to pass only through the lens. The lens support may be rotated at a rate in the range from 1 rotation per second to 100 rotations per second. This aspect and any aspect of the invention using a lens support may further comprise adjusting the radial offset between the center of the lens and support axis.

In some embodiments the invention further comprises aiming the lens prior to directing the femtosecond laser beam through the lens. Aiming the lens may comprise directing a low power light through the moving lens so that a visible pattern is projected on the tissue, wherein the orientation of the lens can be adjusted until the visible pattern is located at a desired incision site. Additionally, some embodiments further comprise deflecting the focused beam from the moving lens to follow a path at an angle relative to the axial direction. Deflecting the focused beam typically comprises, but is not limited to, placing a partially reflective mirror in the focused beam to allow viewing of the eye tissue through the mirror. Such a mirror may be at 45° relative to the axial direction.

In some embodiments this 45° mirror becomes a two axis scanning mirror that increases the 3 dimensional scanning ability of the delivery system.

Another aspect of the present invention is a system for performing partial circular treatment patterns by modulating the laser beam on and off during certain segments of the full circular lens rotation. The on-off modulation is preferably achieved with a mechanical laser shutter or electro-optical modulation of the laser beam at the laser engine module.

Another aspect of the present invention is a system for forming a three dimensional incision into eye tissue. In a preferred embodiment the system comprises: a femtosecond laser source which directs a beam in an axial direction, a focusing lens, a lens support which holds the focusing lens in a plane perpendicular to the axial direction and which moves the lens over a two dimensional path in the perpendicular plane. The focusing lens focuses a portion of the beam incident on the lens to a spot size selected to disrupt eye tissue. This preferred embodiment also has means for controlling the depth of focus of the laser spot to create a three dimensional incision within the eye. The laser source of the preferred embodiment comprises a laser which produces a collimated femtosecond laser beam; and means for expanding the beam prior to the beam reaching the focusing lens. The means for expanding the beam may comprise a Galileo telescope with a fixed expansion factor. Such means may alternatively or additionally comprise a zoom expander that allows adjustment of the beam expansion factor. This allows for easy adjustment from overfilling the lens to various degrees of under filling the lens and thereby changing the delivered laser power and numerical aperture of the focused beam resulting in a variation of spot size. As with previous embodiments, adjusting the exit expansion means adjusting (increasing or decreasing) the divergence of the femtosecond laser. As described in above embodiments the means of expanding the beam exit prior the beam reaching the focusing lens may comprise an adjustable Galileo telescope. Such means may alternatively or additionally comprise an adjustable zoom beam expander. The means of adjusting the exit expansion of the beam is adjustable to control the depth of focus of the laser spot with the eye tissue.

In some embodiments, the focusing lens is a single plano-convex or aspherical lens and the lens support is mounted to rotate about an axis parallel to the axial direction and wherein a center of the lens is radially offset from the axis. Furthermore in some embodiments the focusing lens a single aspherical lens that pre compensates beam aberrations that the laser beam experiences as it propagates into the eye. For instance, if characteristic aberrations of a patient's eye are well known or measured, then a custom focusing lens may be ground to compensate for such aberrations. Embodiments of the invention are not limited a single plano-convex or aspherical lens. The invention in various embodiments may use any lens well known in the art. The system may further comprise means for adjusting the distance of the radial offset. The lens support may also comprise an opaque disc which allows the laser beam to pass only through the lens. The system may further comprise a driver which is adapted to rotate the support about the axis at a rate in the range from 1 rotation per second to 100 rotations per second. Some embodiment also further comprises a means for adjusting the distance of the radial offset.

In the same fashion as the method described above the system embodiment comprises a mirror for deflecting the focused beam from the focusing lens in a lateral direction relative to the axial direction. Typically the mirror is generally oriented at 45° relative to the axial direction and preferably reflects light at the wavelength of the laser beam but allows visible light to pass therethrough.

Some embodiments may further comprise a low power light source oriented to direct a light beam along a path coincident with the path of the femtosecond laser beam, wherein the low power light source can be used for aiming the focusing lens. In some embodiments the femtosecond laser source comprises a femtosecond laser mounted in a free standing cabinet, wherein the system further comprises a support arm having a proximal end attached to the cabinet and a distal end attached to a housing which holds the focusing lens, the lens support, and the depth control means. Another exemplary aspect of preferred embodiments is that the lens support is adapted to be coupled to a microscope, wherein the microscope is oriented to view the eye tissue to be treated. In any embodiment of the invention, the laser treatment system may be mounted or otherwise incorporated into a surgical microscope. In exemplary embodiments, the lens support of the system may be mounted on a surgical microscope where its location can be switched between a disengaged and engaged position under the microscope.

Yet another aspect of the invention is a phacoemulsification machine. This aspect comprises at least the following elements: a housing, a pump and controller located within the housing for delivering a fluid to an eye capsule to emulsify a lens within the capsule, a femtosecond laser located within the housing, a support arm having a proximal end secured to the housing and distal end postionable in a space surrounding the housing, and a laser delivery system secured to the distal end of the support arm wherein the laser delivery system is adapted to deliver focused laser light from the femtosecond laser to the eye capsule.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The invention described relates to techniques apparatus, and systems for laser eye surgery or laser assisted eye surgery. Specifically described herein are methods and systems for delivering a focused femtosecond laser beam into the eye of a patient.

Figure 1:
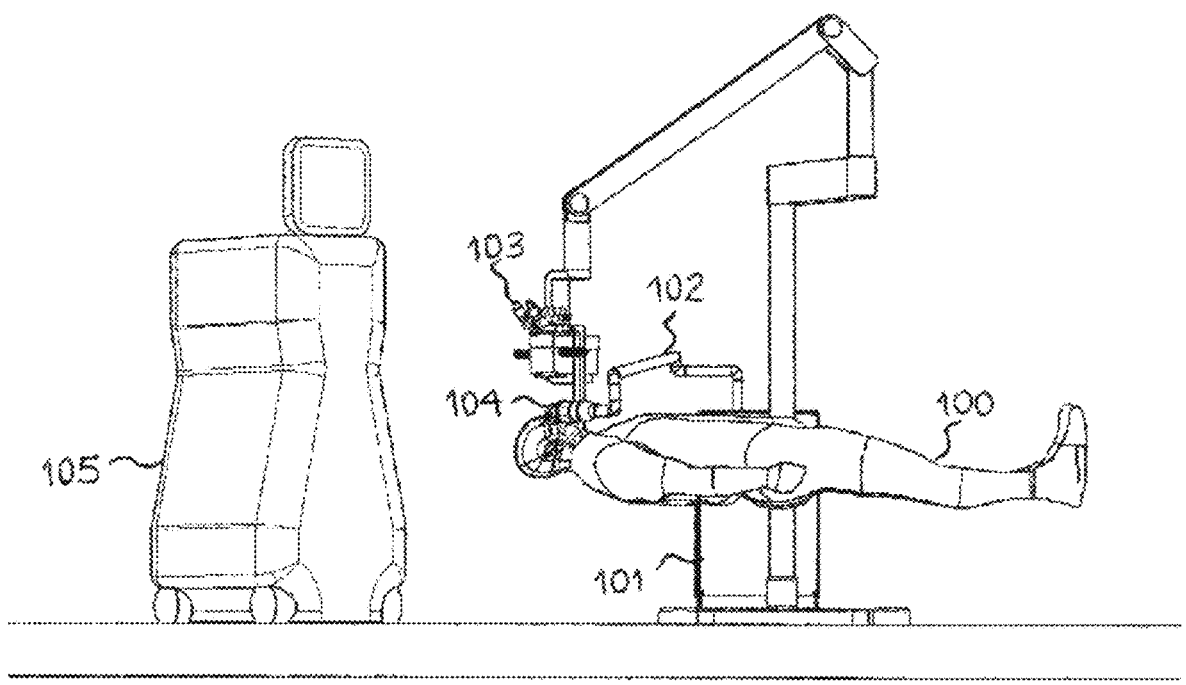
FIG. 1 shows an overview of the laser delivery system.
Figure 2:
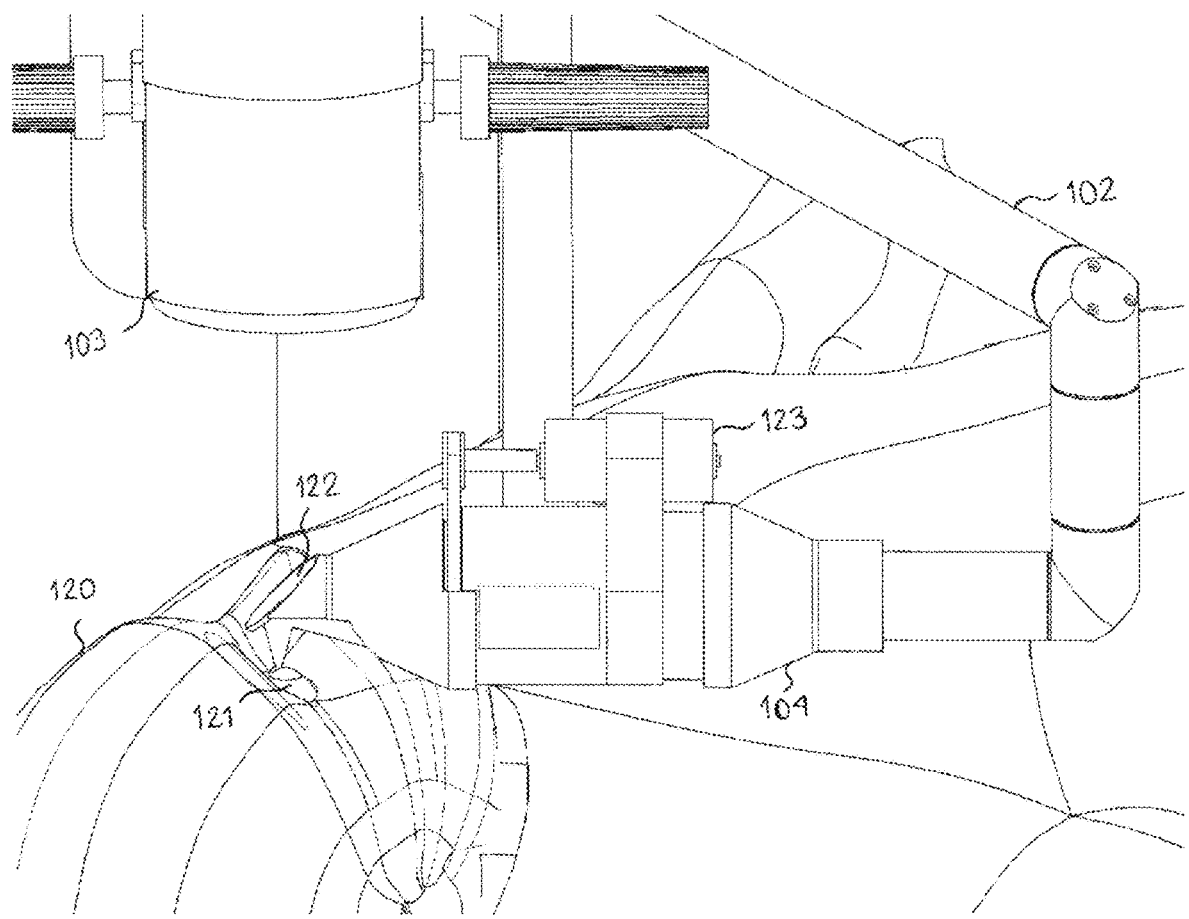
FIG. 2 shows a more close up view of the laser delivery system.
Figure 3:
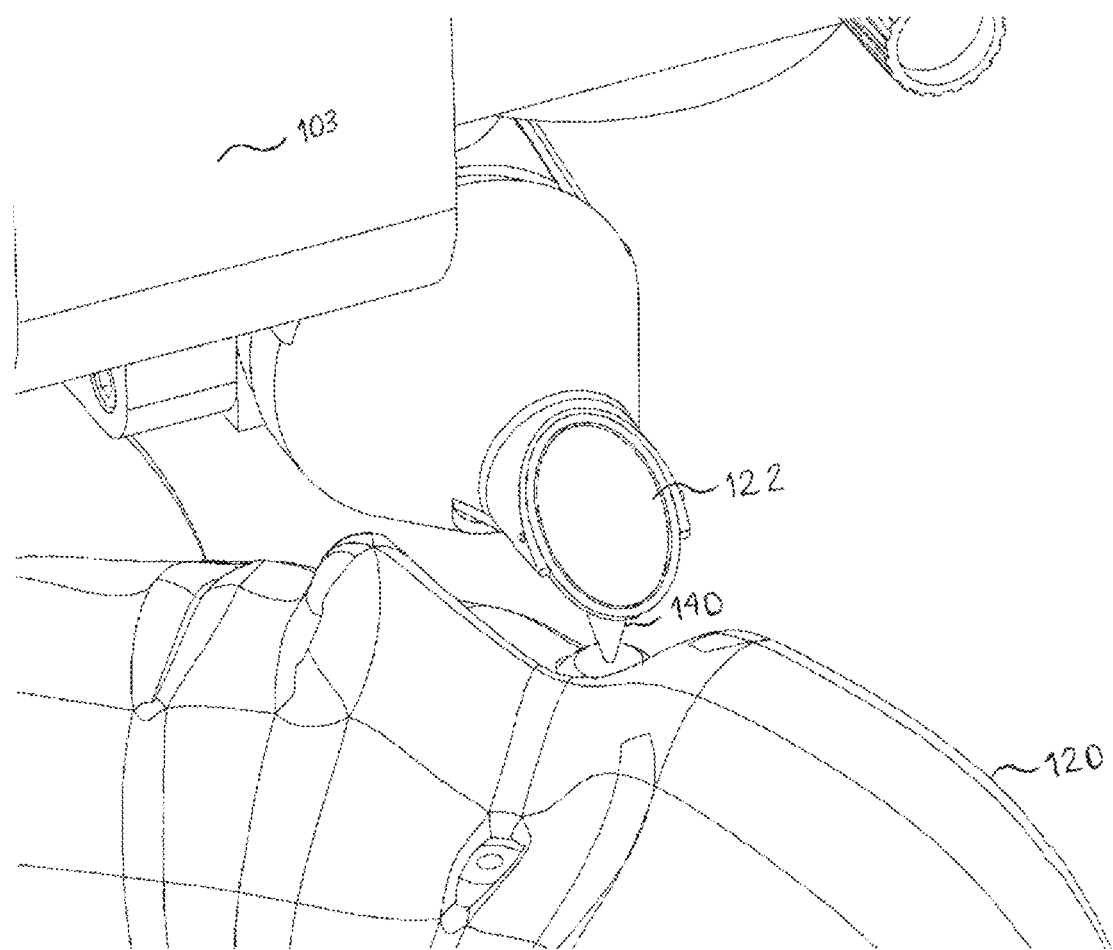
FIG. 3 shows a different angle close up of the laser deliver system.

An exemplary embodiment of the invention is shown in FIG. 1. FIG. 1 shows a system overview of the laser delivery system optics (104) integrated into a typical ophthalmic surgical microscope 103. The delivery system optics unit 104 connects to the laser engine 101 that is placed here next to the microscope stand through an articulating arm 102 that allows propagation of a laser beam. The patient 100 lays in a standard position typical for cataract surgery. The overview is completed by illustrating a typical size phacoemulsification machine 105 close to the surgical microscope. A closer view of this exemplary embodiment is shown in FIG. 2. This view shows the right eye being treated. The left eye is treated by moving the delivery system 104 onto the other side of the microscope 103. In this configuration the articulating arm 102 will simply move further back over the laser box 101. The final 45 degree laser mirror 122 is coated to only reflect the laser wavelength down into the eye. Its coating makes it mostly transmissive for visible wavelengths, so that the surgical microscope 103 view is maintained through this mirror without any significant distortions. The mounting of the optics until 104 is adjusted such that the center of the 45 degree mirror 122 fall into the central optical axis of the microscope 103. The optics unit 104 moves together with the microscope head. It allows for some clearance over the patients eye 121 and away from the patients nose. FIG. 3 shows a different angle view of the 45 degree mirror 122. It illustrates a typical spacing above the patient's eye and illustrates a highly focused laser beam 140 entering the eye.

Figure 4:
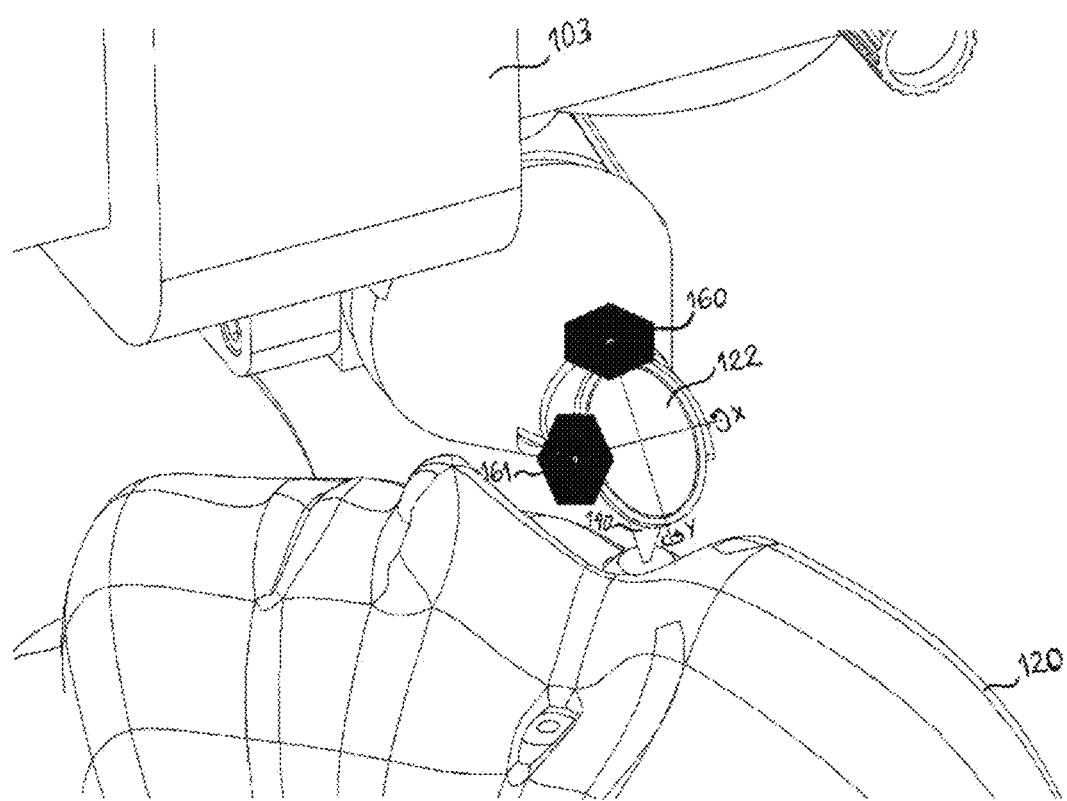
FIG. 4 shows another version of the delivery system

FIG. 4 shows another version of the delivery system were the final 45 degree mirror is mounted in a gimbal mount that allows the mirror to be actuated around the x-axis and y-axis. This actuation is preferably done with galvo scanners 160 and 161 or other rotational motors. This actuated 45 degree mirror allows scanning of the laser beam 140 in a 2-dimensional plane parallel to the iris plane of the eye. Together with the rotating lens 182 and the z-scanning lenses 244 the actuated mirror significantly expands the scanning ability of the system without introducing any significant beam aberrations.

Figure 5:
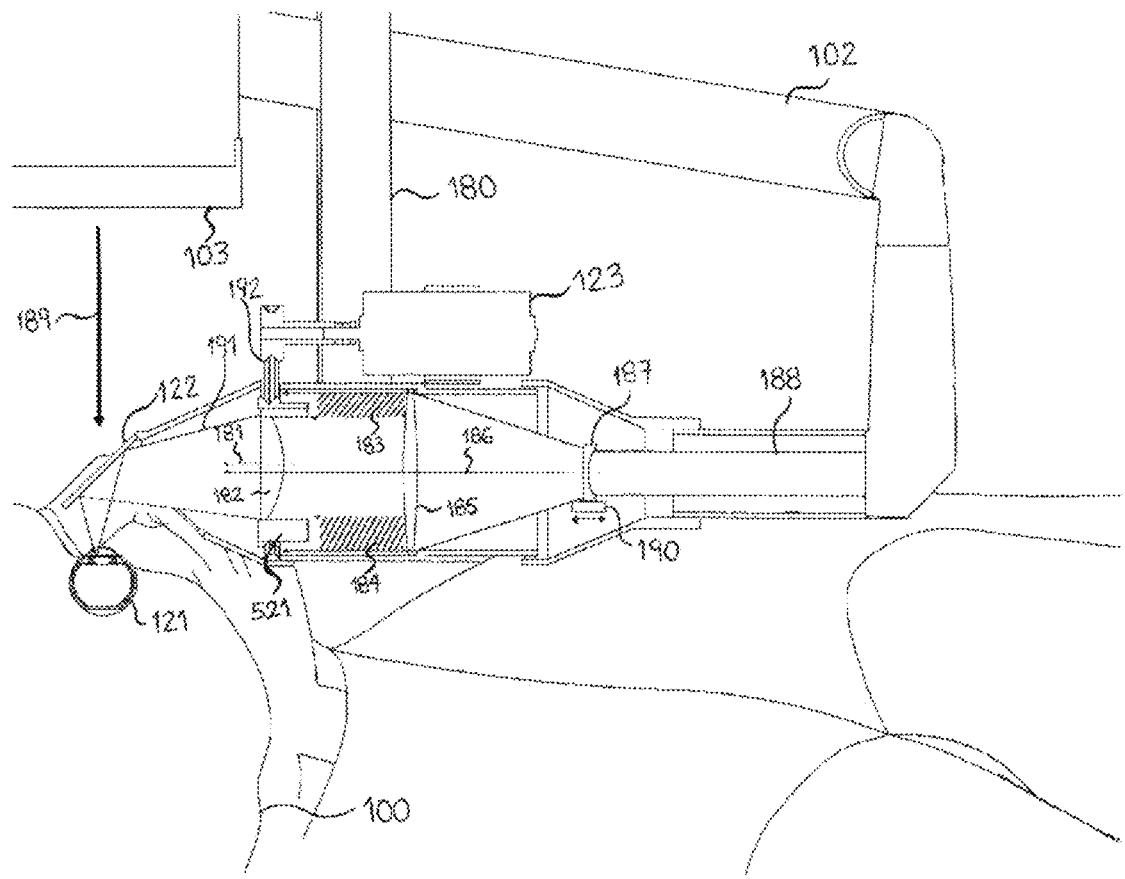
FIG. 5 shows a detailed view of the optics unit.

FIG. 5 shows a detailed view of the optics unit 104. A collimated laser beam 188 enters the unit on the right. The laser beam 188 propagates through a beam expander consisting of 2 lenses 187 and 185. These 2 lenses create in this preferred version a Galileo telescope with the first lens 187 mounted on a linear motorized drive stage 190. This controlled movement of lens 190 or alternatively lens 185 parallel to the laser beam 188 allows the exiting expanded beam 191 to be slightly more or less converging towards its focus point in the eye. This variation in convergence angle of 191 results in an effective z-scan of the laser focus within the eye 121. The focusing lens 182 is mounted in a rotational mount 521, being rotated in a circular way, driven by a motor 123 and a drive mechanism 192. Depending on the treatment laser parameters such as the repetition rate of laser pulses and the desired treatment circle speed the rotating speed of lens 182 can be adjusted with the motor 123. Typical rotational speeds will be between 1 to 100 full rotations per second. The rotational mount 521 either mounts the lens with a fixed offset or a manual adjustable offset amount (adjusted before the procedure) or a motor driven continuously adjustable offset amount that can be adjusted either before or during the treatment procedure. The mount 521 includes a fixed or automatically adjustable counterweight to compensate the offset lens mass and maintain full rotational balance at any time.

Figure 6:
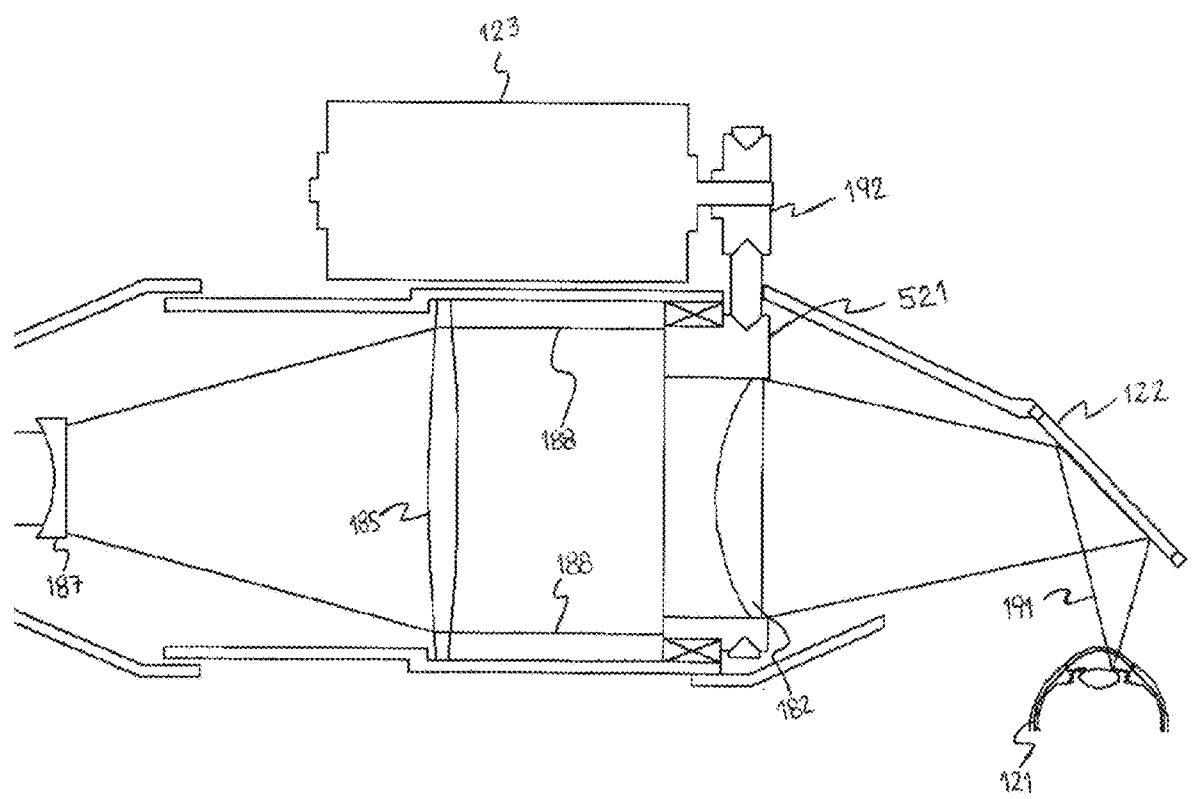
FIG. 6 shows a detailed view of the main treatment laser beam.

FIG. 6 gives another detailed view of the main treatment laser beam path through the delivery system unit 104. The treatment beam 188 is shown propagating through the beam expander lenses 187 and 185 and then being clipped to a smaller beam size as it propagates through the focusing lens 182 and then is being focused as 191 into the eye via the 45 degree flat mirror 122.

Figure 7:
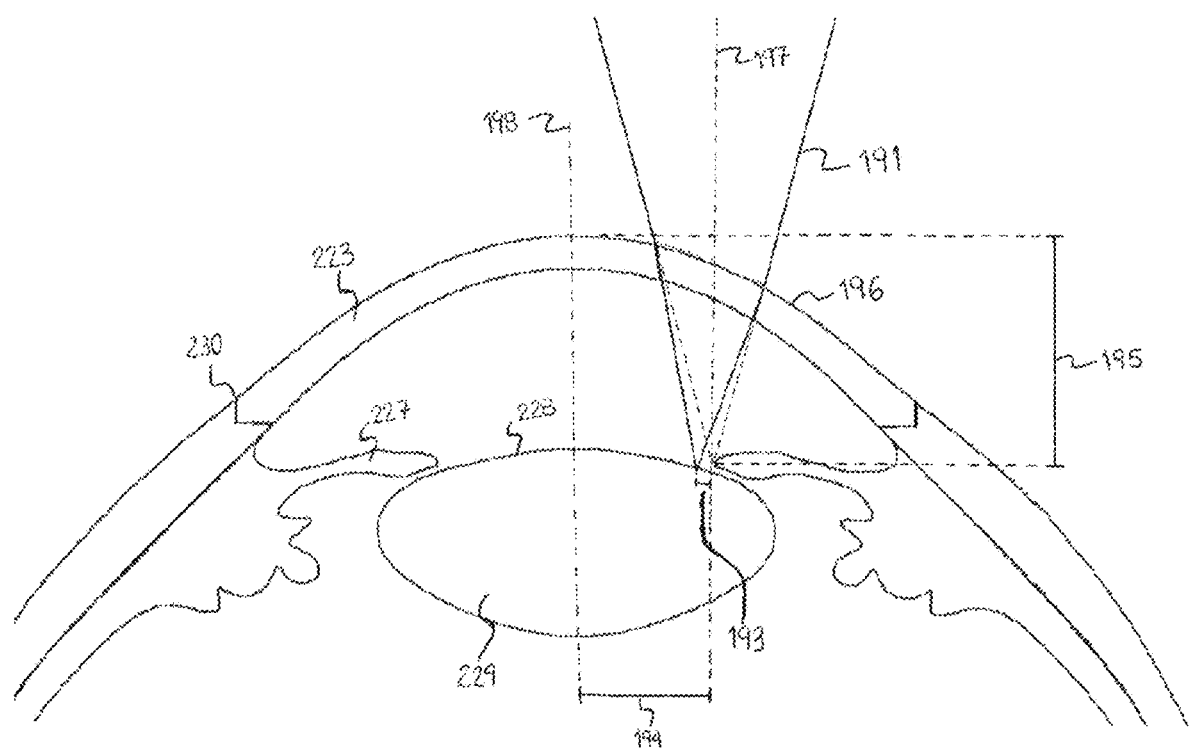
FIG. 7 shows a focused laser beam entering the eye.

Even though the here introduced delivery system minimizes beam aberrations by design some remaining aberrations need to be considered. As shown in FIG. 7, when the focused beam 191 enters the eye through the curved cornea surface interface 196 and to a lesser extend through all eye internal surfaces that the laser propagates, the focusing parameters of the beam are changed. This shifts the focus distance in the vertical axis to a new distance 195. This shift in focus does not need to be compensated for if a aiming laser beam pattern is used to target the desired tissue, since the aiming laser beam is always collinear to the treatment beam and will experience almost the same shift. Therefore adjusting the target area with the aiming beam Furthermore if the beam centerline 197 has an offset 194 to the centerline of the eye 198 the beam focus experiences a slight shift 193 towards the center of the eye. The amount of shift depends on how deep the focus is placed within the eye 195 and at what radial distance 194 from the centerline 198 the beam enters the eye. This shift can be easily measured and calculated for any given offset number and can therefore be compensated for if desired. The shift furthermore effects the aiming beam in the almost same amount (except for a small wavelength dependency) and is therefore already anticipated and included in the visual alignment of the target zone.

The radial offset 194 creates spherical and other higher order aberrations that reduce the beam quality and therefore enlarge the achievable spot size inside the eye. The aberrations can however be measured and calculated for any given offset and can effectively be eliminated by a custom shaped focusing lens 182 that pre compensates for the aberrations. For example, if a circular capsulotomy scan pattern is performed with a cutting diameter of 5 mm diameter, then the aberrations induced by the corresponding 2.5 mm radial offset 194 can be pre measured and a custom shaped focusing lens 182 can be used to pre compensate these aberrations. As the focus moves in a circle inside the eye, the focusing lens rotates accordingly so that the direction of the custom shape of the lens 182 is always in the correct direction to compensate the aberrations at any moment during the entire rotation.

Figure 17:
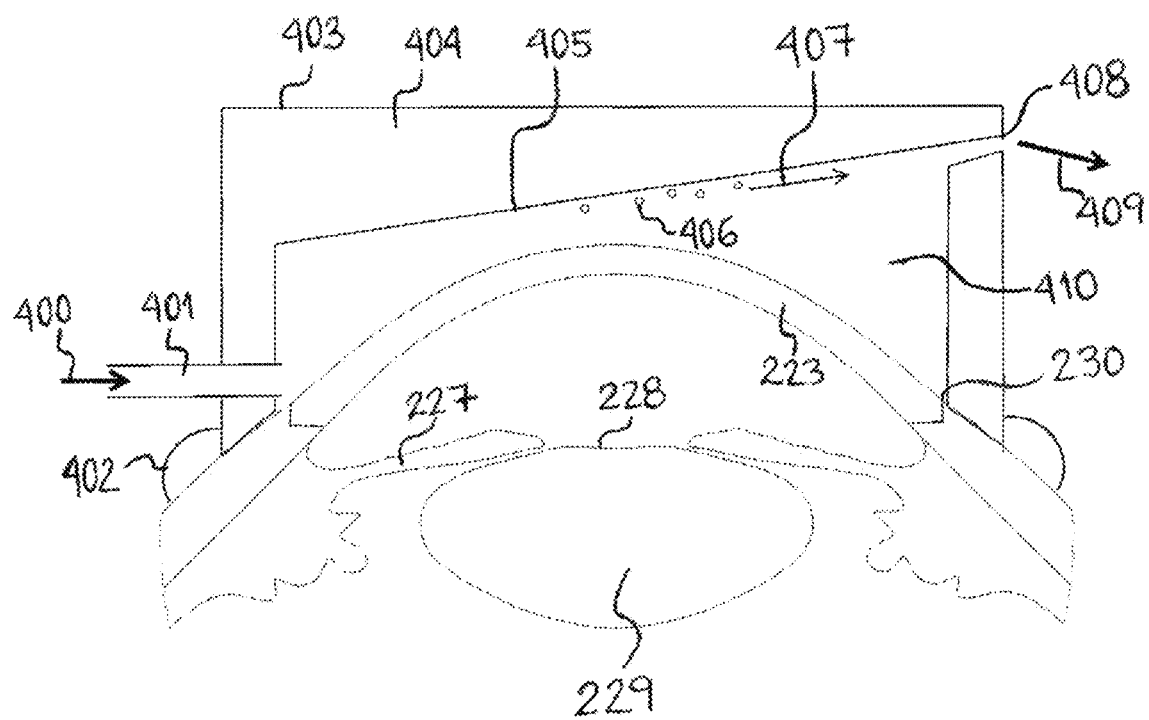
FIG. 17 shows a custom contact lens that reduces aberrations
Figure 18:
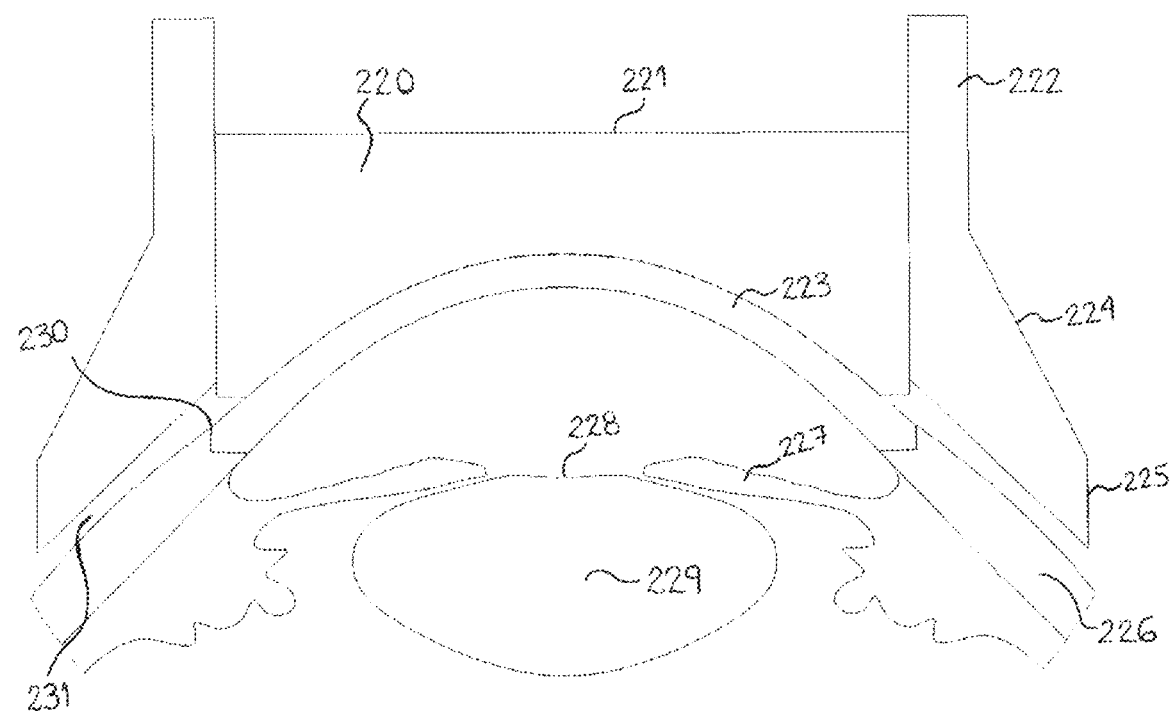
FIG. 18 shows a further embodiment of a custom contact lens

Another way to reduce or eliminate these aberrations without the need for a custom shaped focusing lens 182 is by using a custom contact lens as shown in FIGS. 17 and 18. These lenses are placed on the eye and provide a flat upper surface that essentially eliminates the above described aberrations and shifts. These contact lenses can be full patient interfaces connecting the eye to the delivery system or are preferably designed to not connect to the delivery system unit and do not change any of the above described contactless design systems and methods.

Figure 8:
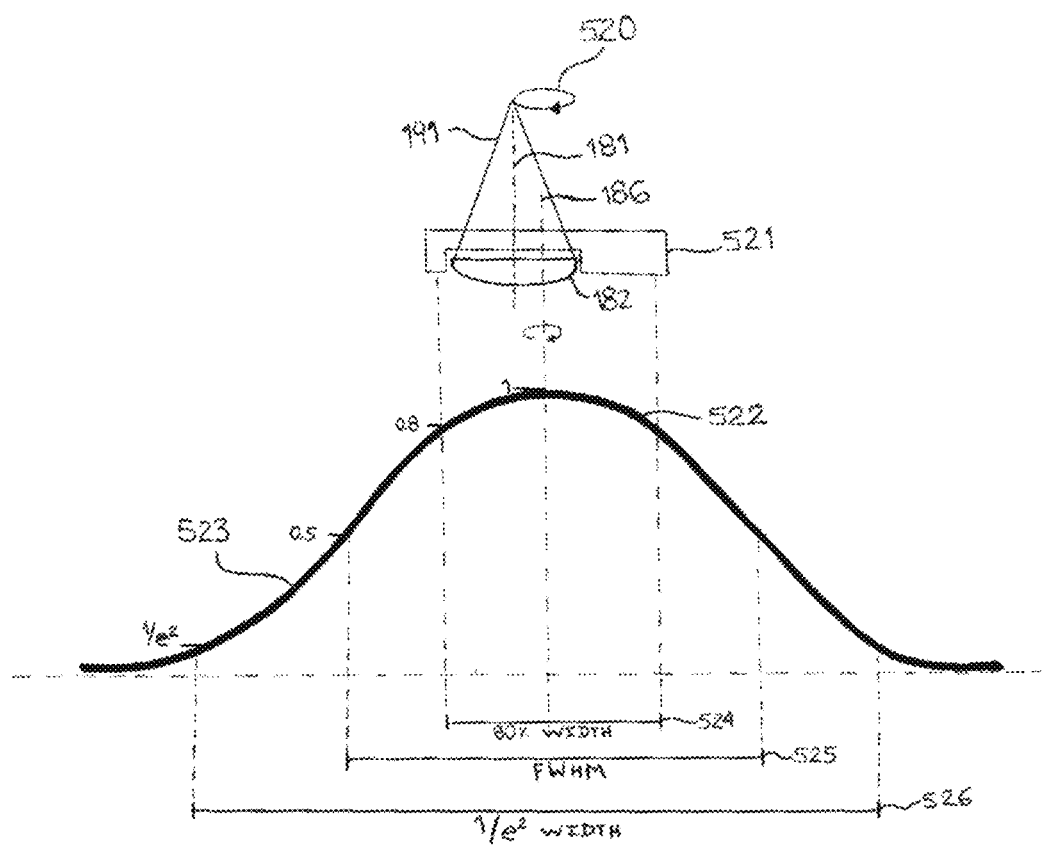
FIG. 8 shows the treatment laser beam intensity profile.

FIG. 8 illustrates the treatment laser beam intensity profile 523 as it overfills the rotating focusing lens 182 mounted inside an offset mount 521. The laser beam center line 186 is also the rotational axis of the lens mount. To achieve sufficient beam homogeneousness over the entire focusing lens area and during the entire lens rotation an adequate overfilling ratio is selected. In the here shown overfill selection the entire lens through all of its rotational positions stays within a 80% intensity beam width 524 portion 522 of the Gaussian laser beam 523. Limiting the lens position to that central laser zone creates nearly uniform intensity profile since this top intensity curve 522 section is relatively flat. Depending on how uniform the intensity profile is desired, the beam overfilling amount can be increased or reduced. Depending on the laser beam coherence quality, If the laser beam starts out more like a flat top profile versus a perfect Gaussian profile then less overfilling is required to achieve the same homogeneous intensity profile. The focusing beam 191 shows the portion of the incoming laser beam that gets focused onto the target plane. 520 illustrates the scanned focused circle that is achieved through the rotating lens. The lens offset can be adjustable and is here shown by the distance between the central lens axis 181 and the central system and incoming beam axis 186. More typical laser beam width definitions such as full width half maximum FWHM 525 and $1/e^2$ diameter 526 are also illustrated as a reference here.

Figure 9:
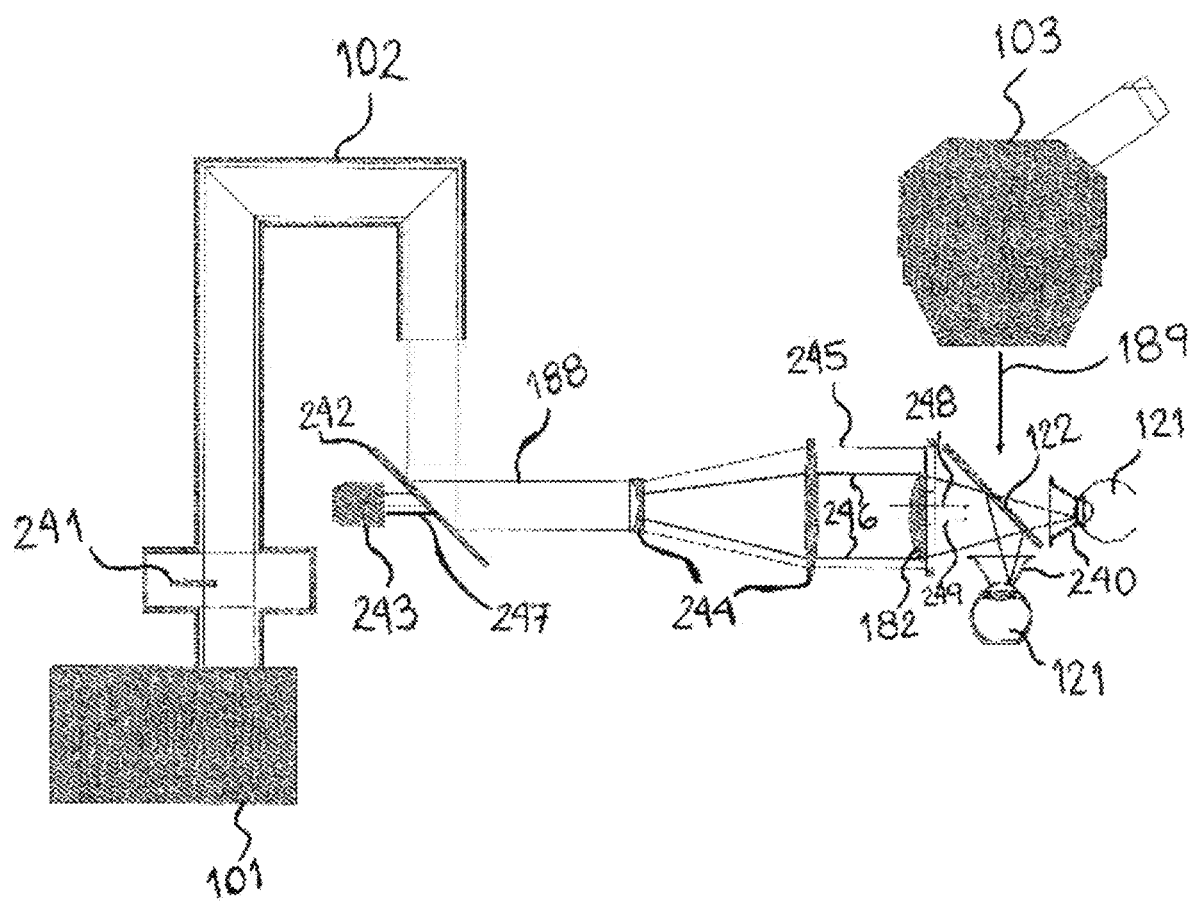
FIG. 9 shows a further embodiment of the laser delivery system.

FIG. 9 illustrates further details and embodiments of the here disclosed laser delivery system. The rotating lens 182 is shown here in its momentary lowest position. The offset can be seen between the central system axis 248 and the central lens axis 249. This offset results here in the laser focus being placed inside the lower eye 121 on the right side. The 45 degree mirror 122 is here shown as optional. It is used when the delivery system is integrated under a microscope 103 with the central viewing axis 189 going approximately through the center of the mirror 122. In this configuration the 45 degree mirror 122 reflects the laser wavelength, but let's enough visible light through such that diagnostic beams can go through it in transmission. Therefore the 45 deg mirror 122 can be used next to the eye to reflect the laser beam into the eye and thereby allowing the use of a standard surgical microscope 103 or integration into a slit-lamp microscope system. The microscope viewing path 189 is used for observation, video visualization and diagnostics beams of the eye, before and during the laser treatment procedure also referred to here as laser firing. Furthermore a feedback beam can be coupled with the optical path of the delivery system before the beam expander by using a beam splitter or partial mirror such as mirror 242. This feedback beam is used for diagnostics, calibration, targeting and controlling of the laser settings, including laser on/off control. This feedback beam can be activated and used before and during the laser treatment procedure. It can enter and exit the optical path of the delivery system just like the beam 247 is illustrated in FIG. 9. Note that 247 here also represents the aiming beam coming out of the module 243. The delivery system can also be operated in a straight way without a 45 degree mirror. This version can be used in an office setting where the delivery system is integrated with a slit lamp. Furthermore a optional patient interface 240 is illustrated that creates a hard docking connection between the eye and the delivery system. The preferred embodiment uses no hard connected patient interface and there is no contact between the delivery system and the eye. To reduce aberrations and to improve eye fixation several patient interfaces, here also referred to as custom eye contact lenses are described later. If they are only connected to the eye and do not make any contact to the delivery system then it is therefore still considered a contactless approach in the sense that there is no contact between these contact lenses and the delivery system and therefore no docking takes place. FIG. 9 illustrates both: (a) a system for a fully docked procedure where the patient interface 240 is used and where it is ultimately docked and thereby connected to the rest of the delivery system and (b) a system where either a patient interface 240 is not used or it is used, but not docked and therefore not connected to the rest of the delivery system The non-docked case is also illustrated in FIG. 3, FIG. 5, and FIG. 6. The contact lenses or patient interfaces described in FIG. 17, FIG. 18, FIG. 19, and FIG. 20 are shown in a non-docking configuration, just connected to the eye.

Figure 10:
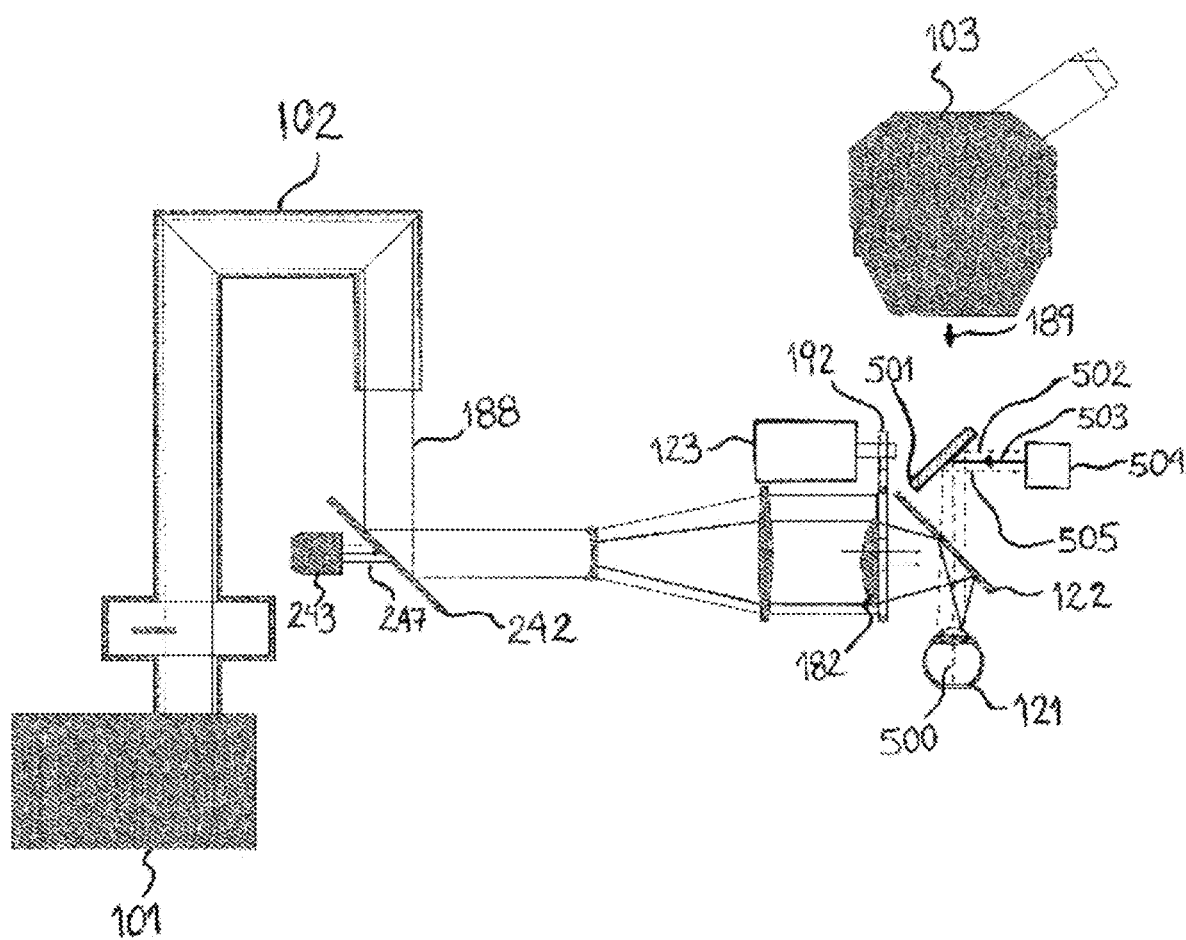
FIG. 10 shows another embodiment of the laser delivery system.

FIG. 10 shows further embodiments and details of the delivery system. Above the 45 degree mirror 122 is another optional 45 degree mirror 501. It is also transmitting most of the visible wavelengths so that the microscope 103 view 189 is no much affected by it. Its purpose is to reflect a eye fixation light beam 503 coming from the illumination grid unit 504. The delivery system is adjusted over the eye 121 so that the eye fixation light beam 503 becomes the central axis beam through the patient's eye 121. The patient will fixate his eye by keeping this light in his central view either during docking if a patient interface 240 is used or during the entire procedure if no patient interface is used. The illumination grid unit 504 further produces light pattern beams 502 that create a visible grid pattern on the outer or inner surfaces of the eye. These grid patterns are used by the surgeon to center the eye or treatment zone(s).

The aiming beam module 243 includes a low power aiming beam laser and beam shaping optics that allow for a fixed or adjustable laser beam diameter. The size of the aiming beam diameter determines the spotsize of the aiming beam pattern in the target region of the eye. According to Formula 1, a large aiming beam diameter will result in a large focusing angle and small spot size. This will increase the sensitivity and resolution in the z-axis adjustment of the microscope connected to the delivery system unit 104 and allows for a more precise z-plane detection by focusing the aiming beam pattern (circle) onto a surface interface of or within the eye. This interface could for example be the top or bottom surface of the cornea, the anterior or posterior capsule surface, the iris plane or other interfaces. The preferred aiming beam diameter is 20% to 80% of the collinear treatment beam diameter.

The aiming beam 247 is collinear overlapped to the treatment laser beam 188 through a 45 degree mirror 242 with a dichroic coating. For easier diagram readability it is here only shown until the mirror 242, but it does continue collinear to the treatment beam throughout the entire optical system. The collimation angle of the aiming beam is adjusted within the optic unit 243 such that the focus plane of the aiming beam in the eye is vertically offset to the focus plane of the treatment laser beam. This offset can be adjusted in both directions to achieve an up or down focus plane offset in the z-axis.

Figure 11:
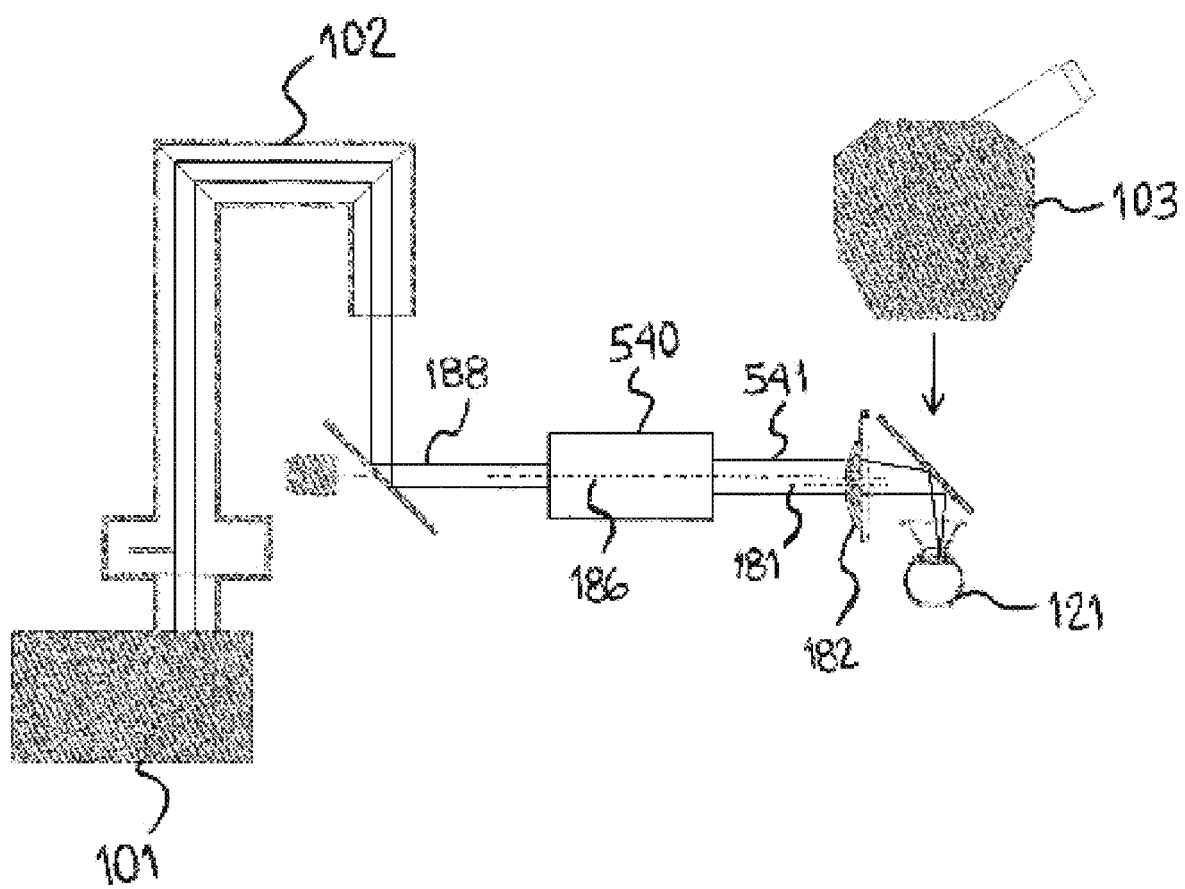
FIG. 11 shows another embodiment with a general beam expander.

FIG. 11 shows further embodiments and details of the delivery system. Here the beam expanding unit that was shown in FIG. 008 as a Galileo Telescope with the lenses 244 has now been replaced with a general beam expanding unit 540 that allows fixed or adjustable (with a zoom lens system) expansion factors. The expansion amount can be adjusted from overfilling as described in FIG. 007 to under filing the lens 182 shown here in FIG. 011. The beam diameter 541 exiting the expansion unit 540 is here set so small that it always remains within the lens 182 area while the lens rotates around the central axis 186 with an offset illustrated by the central lens axis 181. In this version all of the laser power is delivered to the target spot and none of the beam is clipped during the rotation of the lens. This smaller beam going through the focusing lens 182 results in a larger spot size compared to a fully or overfilled lens 182. It does however not change the position of the focus inside the eye. This configuration is chosen when the priority lays in delivering more laser power to the eye versus achieving a minimum spot size. By using an adjustable zoom beam expander unit 540, the spot size and beam delivery power (if clipping occurs) can be adjusted before the laser treatment or during the laser treatment procedure. The resulting change in beam diameter 541 before the focusing lens 182 results in a changing focusing angle Θ and according to Formula 1 in a changing focus size diameter 2×ω0.

Figure 12:
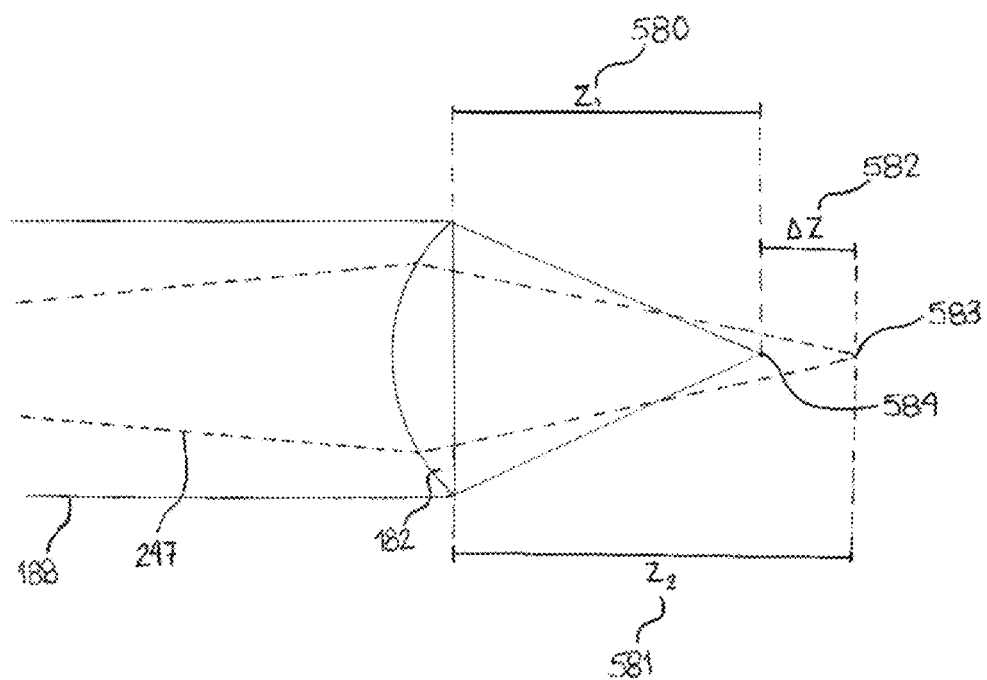
FIG. 12 Illustrates the effect of a slightly more diverging collimation angle of the aiming laser beam relative to that of the treatment laser beam.

FIG. 12 illustrates the effect of a slightly more diverging collimation angle of the aiming laser beam 247 relative to the treatment laser beam 188. Both beams go through the same focusing lens 182. This results in a focus plane shift between the two lasers. The treatment beam 188 is focused in spot 584, which is closer to the lens than the focus spot 583 of the aiming beam 247. The aiming beam focal plane is shifted further away from the focusing lens 182 by the amount of delta Z 582.

Figure 13:
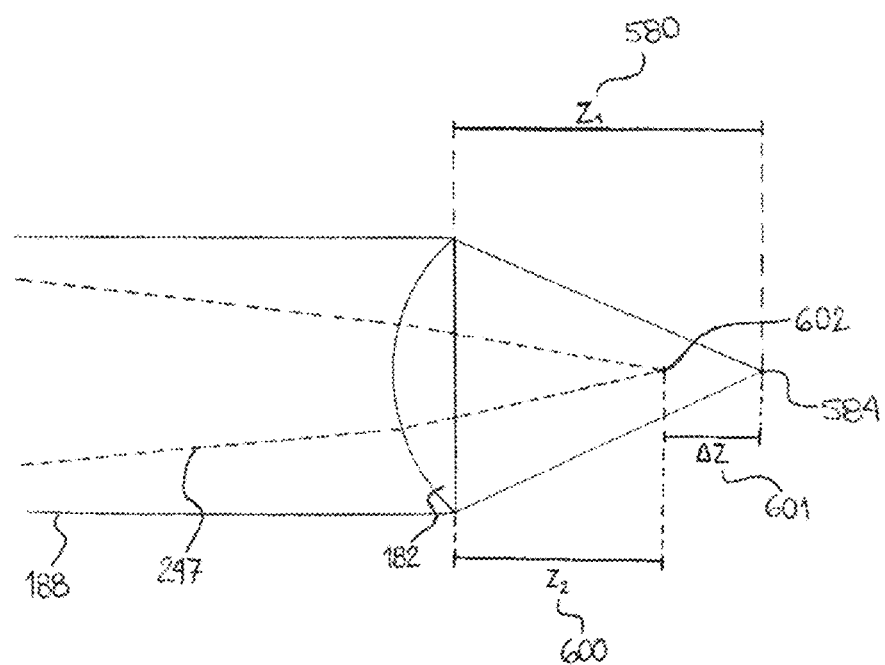
FIG. 13 Illustrates the effect of a slightly more converging collimation angle of the aiming laser beam relative to that of the treatment laser beam.

FIG. 13 illustrates the effect of a slightly more converging collimation angle of the aiming laser beam 247 relative to the treatment laser beam 188. Both beams go through the same focusing lens 182. This results in a focus plane shift between the two lasers. The treatment beam 188 is focused in spot 584, which is further from the lens than the focus spot 602 of the aiming beam 247. The aiming beam focal plane is shifted closer to the focusing lens 182 by the amount of delta Z 601.

This design feature is used to align the delivery system with the help of a aiming beam pattern or circle and then fire the treatment laser starting above as illustrated in FIG. 012 or below the aligned plane as shown here in FIG. 013. For example to make a capsulotomy incision with this delivery system, the aiming beam circle (created from a static aiming beam going through the rotating lens 182) is focused onto the surface of the lens capsule. The treatment laser plane starts shifted down by (delta Z). The treatment laser is fired and through an upward z-scan performed with lens 187 the treatment beam is scanned in a upward spiral, cutting through the capsular bag.

Figure 14:
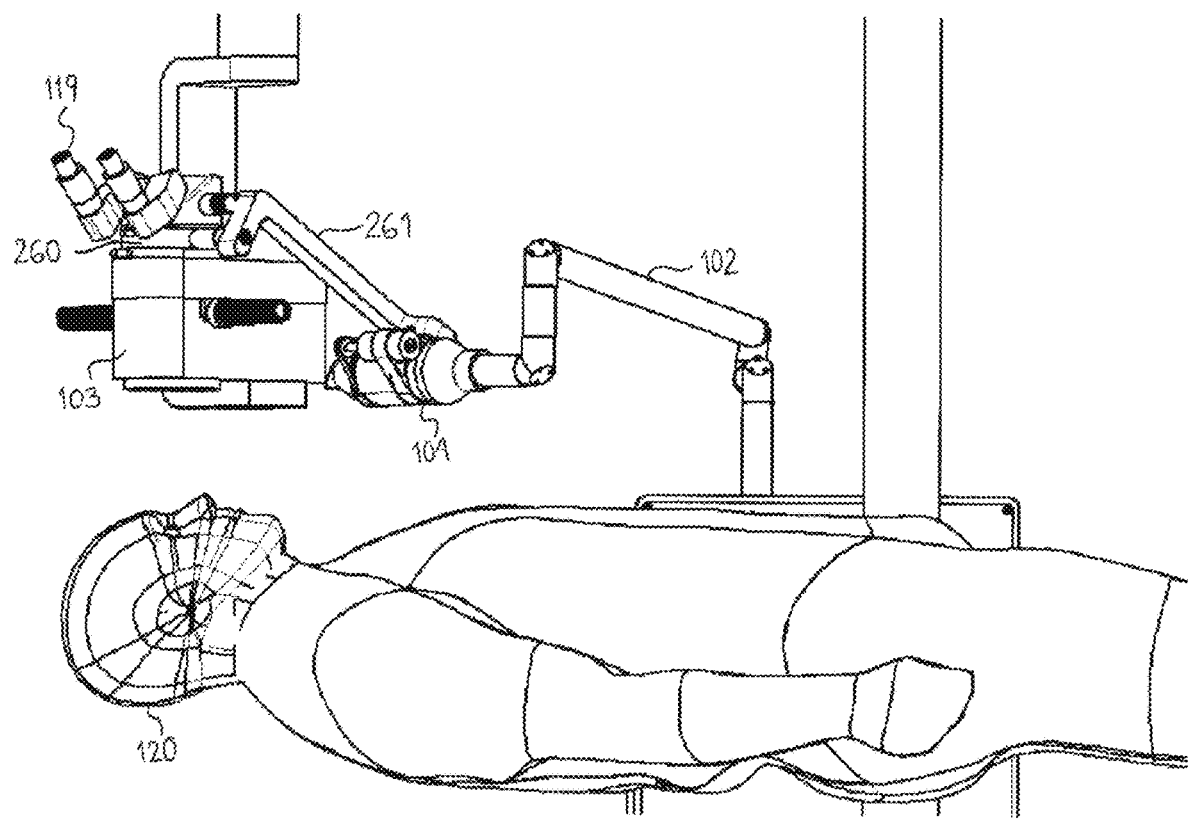
FIG. 14 shows the delivery system unit integrated with a standard surgical microscope in a disengaged (out) position.
Figure 15:
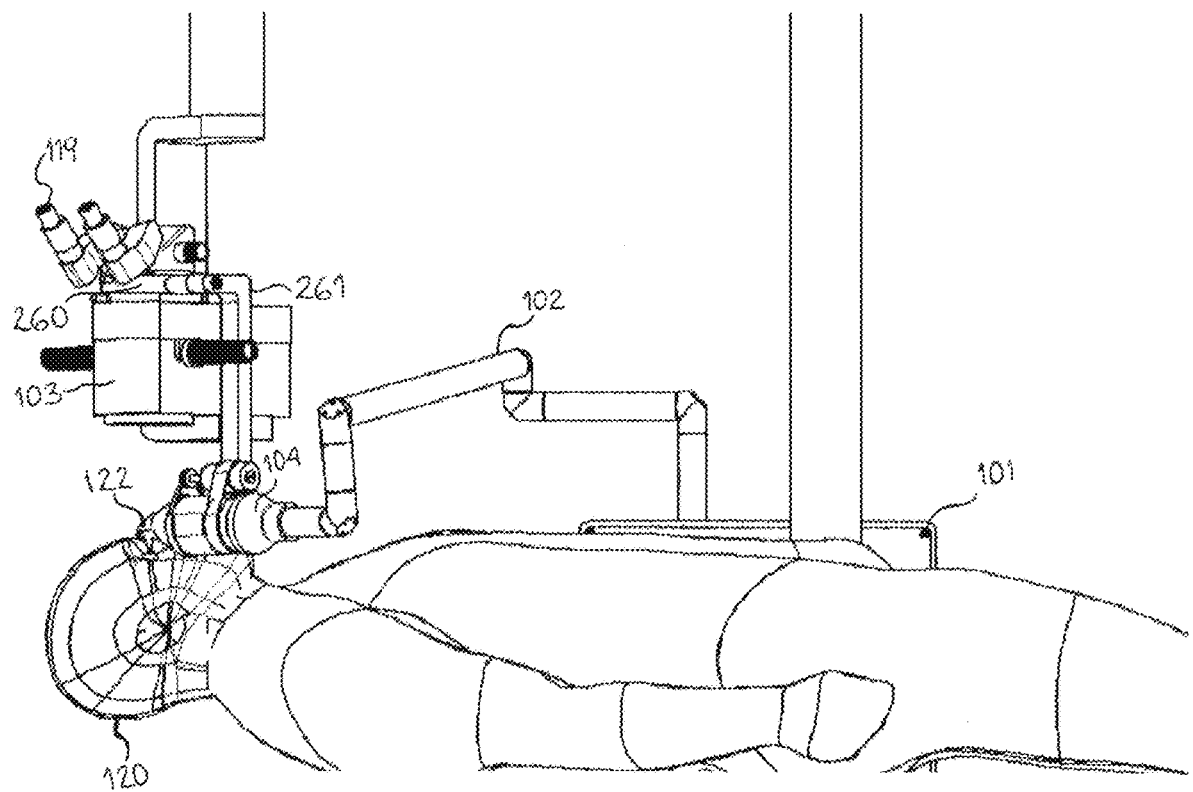
FIG. 15 shows the delivery system unit integrated with a standard surgical microscope in an engaged (in) position

FIG. 14 shows the delivery system unit 104 integrated with a standard surgical microscope 103 in a disengaged position. This position leaves full access for the surgeon under the microscope to perform any standard surgical procedure such as the cataract lens extraction or intraocular lens placement. The delivery system unit is connected to the microscope using a swing arm bracket 261 and a mounting adapter 260 placed below the main surgical view port 119. The swing arm bracket 261 is here shown in its up position for a right eye treatment. FIG. 15 shows the same view with the swing arm bracket locked in its lower position. This makes the system ready for the laser treatment part of the surgery.

The swing arm bracket can be moved during the surgery between the up and down position in a manual way using optional sterile handles or in a preferred version is motorized and can be switched up and down using a single foot or hand switch. The lower position that enables the laser treatment includes a precision referenced stop in all 3 dimensions that assures calibrated distances and assures alignment of the main optical microscope viewing axis to the axis going centrally through the 45 degree mirror 122. The articulating arm 102 allows the delivery system unit 104 to be moved between around with the microscope in both the up and down position without affecting the laser beam alignment entering the delivery system unit 104.

FIG. 14 and FIG. 15 show the microscope integration for a right eye. The left eye configuration can be equally achieved by bringing the mounting bracket 261 to the other side of the microscope head 103. This can be either done manually before the surgery or with a motorized mechanism incorporated in the mounting adapter 260.

Figure 16:
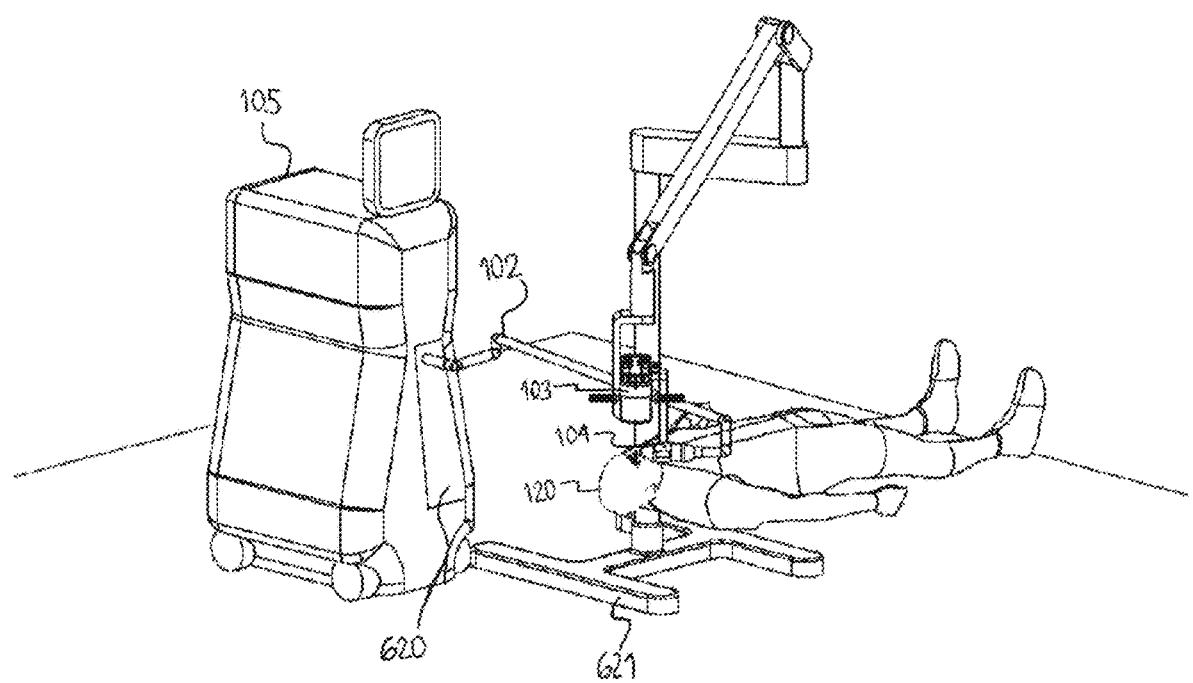
FIG. 16 shows the delivery system unit integrated into a typical phacoemulsification machine.

FIG. 16 FIG. 017 shows another version were a compact laser engine version 620 is integrated into a typical phaco emulsification machine as a sub module 620. The articulating arm 102 is now exiting the phaco machine together with all other power and control lines that are preferably routed along the articulating arm 102. This integrated design allows for a most efficient surgical setup where all aspects of the typical cataract surgery can be controlled by one machine. The laser delivery system unit 104 to microscope 103 integration is identical to FIGS. 014 and 015.

FIG. 17 shows a custom contact lens that reduces aberrations and increases eye fixation while still being non-docking in regard to the delivery system. It is designed to be used in a position where the patient lays on his back and the central eye axis is parallel to gravity. The aberrations are minimized by using a high quality transparent material 404 with a flat top surface 403. The lens is placed along the limbus 230 of the eye. An optional suction ring 402 can be incorporated to increase the connection stability of the contact lens to the eye. This design causes no cornea applanation or significant intra ocular pressure rise due to the liquid inner cell 410.

After the lens has been placed on the eye the inner cell 410 is filled 400 with water or similar liquid through an opening 401 on the lower end of the contact lens. Due to the slope 405 of the inner top surface any remaining air bubbles will be pushed out 409 through an exit hole 408 on the upper end of the contact lens. The water is injected until all air has left the space 410.

Due to this liquid interface a very good refractive index matching is achieved between the material on the top of the contact interface, the liquid in space 410 and the cornea 223. This creates a low aberration entry path of a highly focused laser beam into the eye.

By using this contact lens the rotating focusing lens in the delivery system can be simplified to a standard plane-convex single lens and the laser beam can be scanned with very low aberrations throughout the entire eye.

FIG. 18 shows another custom contact lens that reduces aberrations and increases eye fixation while still being contactless in regard to the delivery system. This design is comprised of a clear material 220 that is either solid and curved to match the radius of curvature of the cornea 223 or is filled with a clear liquid and then stabilized with a flat glass plate 221. In either case the top surface 221 is flat and therefore minimizes aberrations. The lens includes an outer flange 225 that extends over the sclera 226 while maintaining a small gap 231. This gap assures that a good cornea connection of a solid version material 220 is achieved. When a liquid material 220 is used, the gap is then automatically closed and seals the liquid in.

Figure 19:
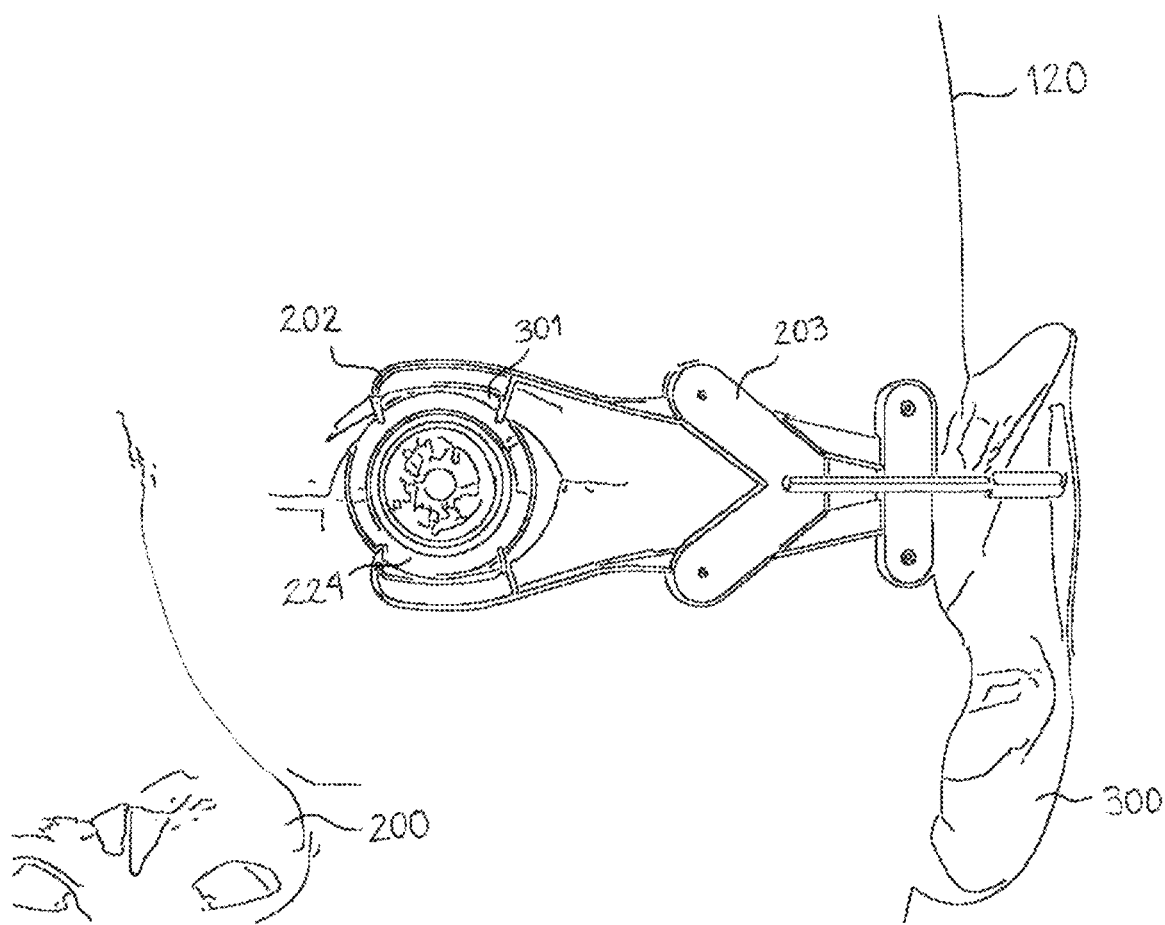
FIG. 19 shows a different view of the custom contact lens.
Figure 20:
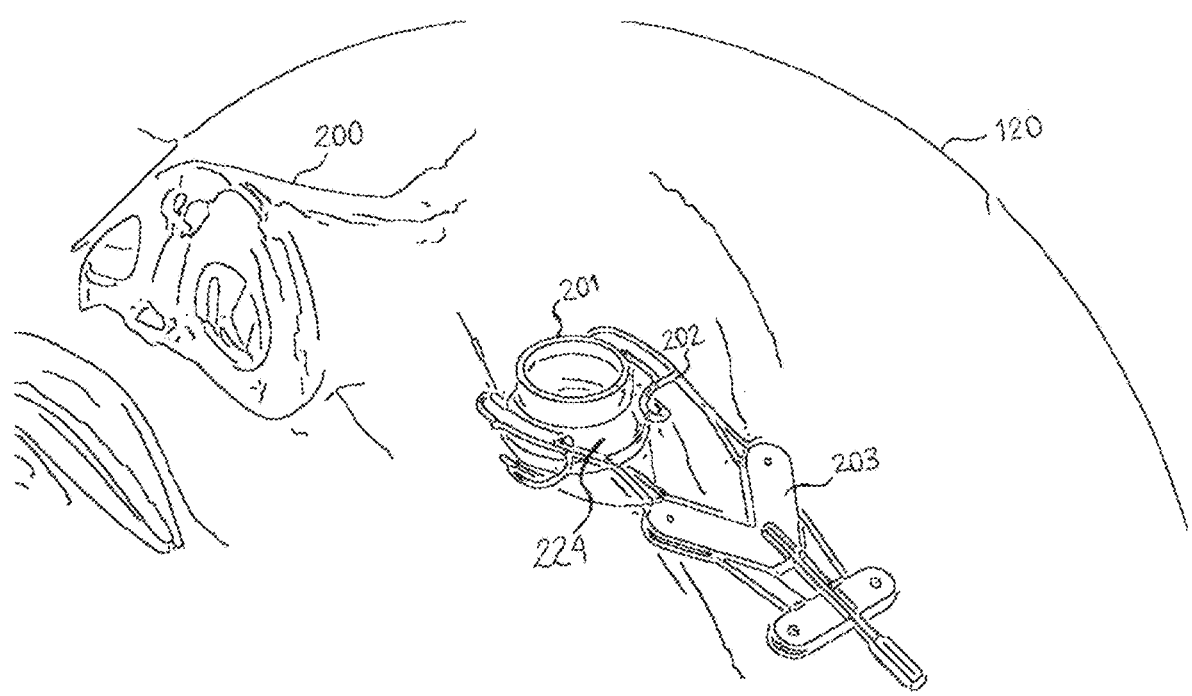
FIG. 20 shows a different view angle of the custom contact lens.

The flange 225 includes an angled slope surface 224 that is designed to interface with a speculum such that the contact lens is slightly pushed downwards towards the eye. This is illustrated in FIG. 19.

The speculum 203 is holding the eye open and in the same time pushes the contact lens towards the eye through a contact of the speculum wire 202 or blade with the sloped surface 224. The amount of down force can be adjusted by the amount of speculum opening and by the design angle of the slope 224. This contact lens creates stable eye fixation and minimizes laser beam aberrations for laser access of the entire eye.

Figure 21:
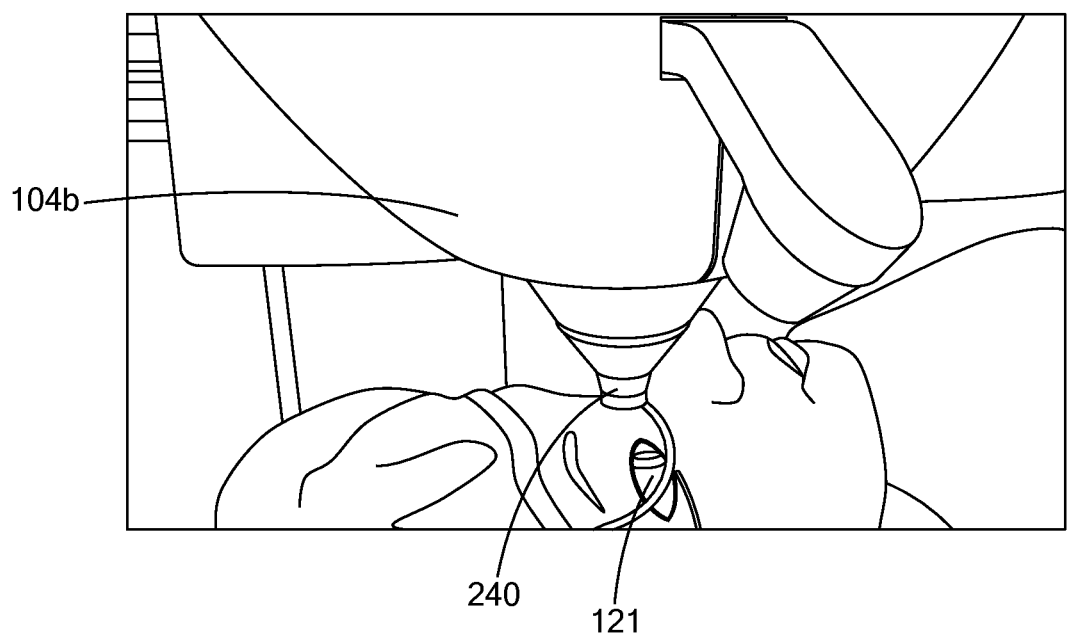
FIG. 21 shows a prior art delivery system as it aligns over the eye before docking

FIG. 21 shows a system of prior art where the patients eye 121 is positioned under a patient interface 240 that is hard connected to the optical delivery system 104b. The picture illustrates the setup procedure just prior to docking the patient interface 240 with the eye 121.

Figure 22:
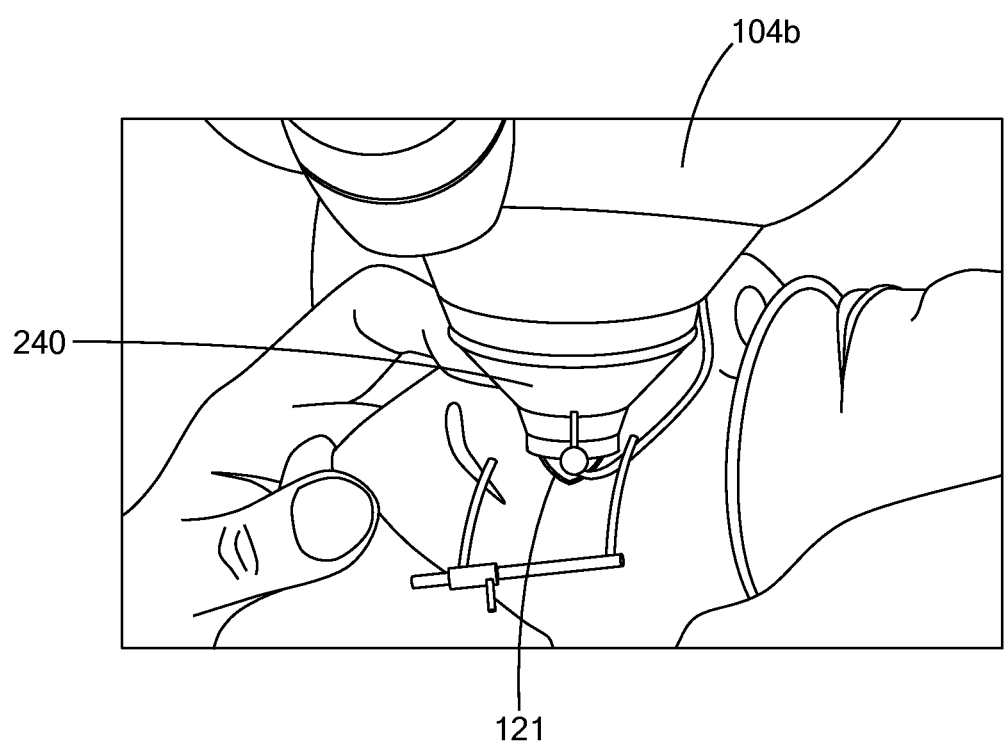
FIG. 22 shows a prior art delivery system after docking of the eye to the delivery system is complete.

FIG. 22 shows the illustration from FIG. 21 right after docking is complete. The patients eye 121 is now fixated under the patient interface 240 which in turn is hard connected to the delivery system 104b.

Figure 23:
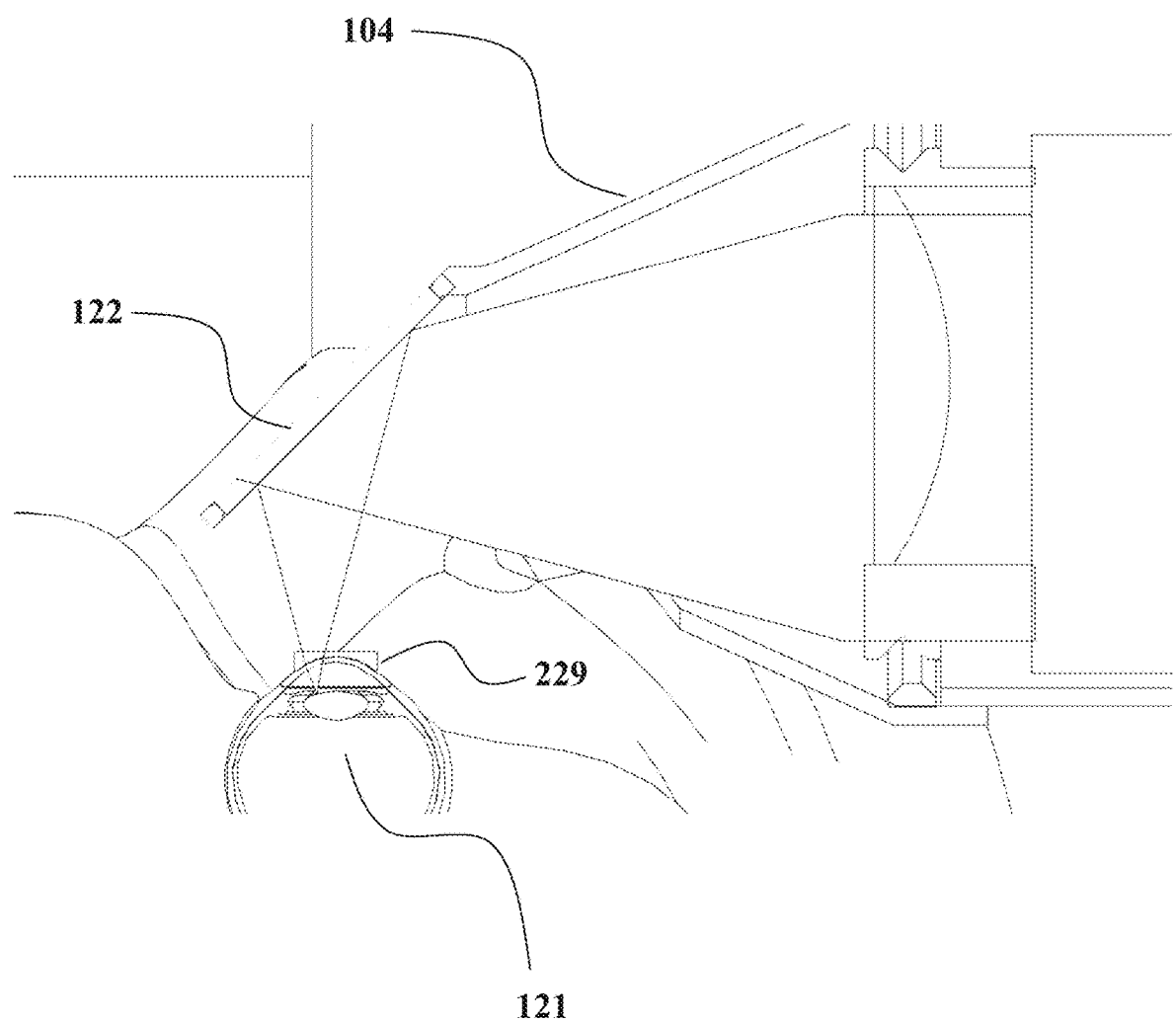
FIG. 23 illustrates the laser beam path through the delivery system and through a non-docking patient interface connected to the eye only.

FIG. 23 shows a cross sectional view of the laser beam path as it propagates through the delivery system unit 104 and onto the 45 deg mirror 122 and into the eye 121. Illustrated on the eye 121 here is a patient interface 229 that is in contact with the eye, but does not make any connection with the delivery system unit 104. This figure therefore illustrates a non-docking surgical setup.

Figure 24:
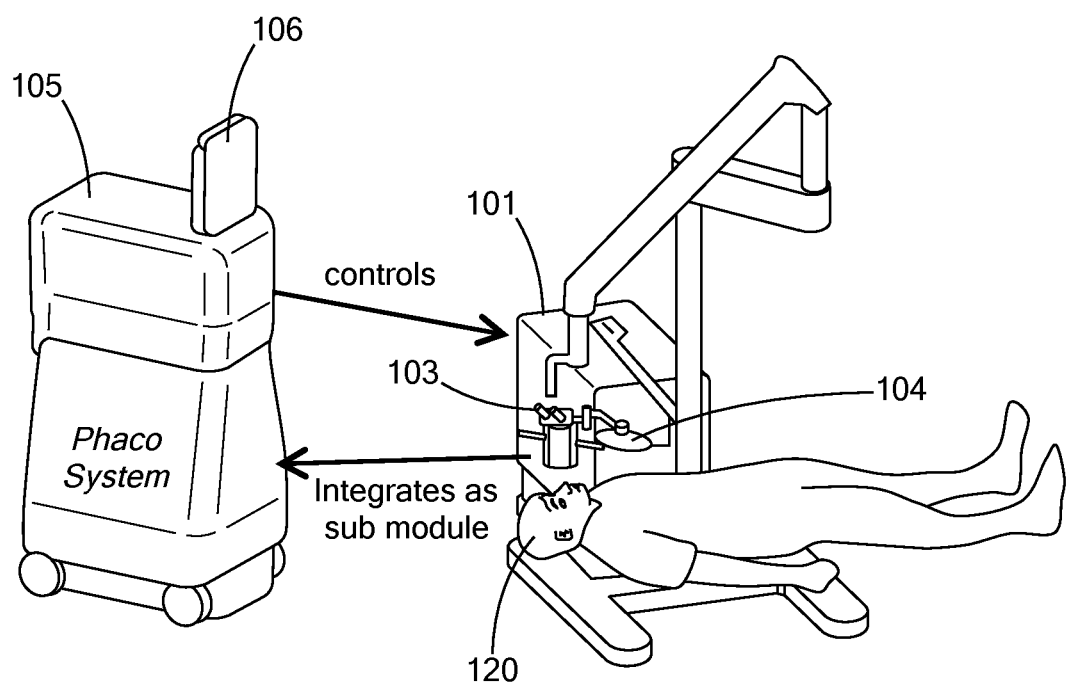
FIG. 24 illustrates various integration and control scenarios between the laser system, a phacoemulsification system and a microscope.

FIG. 24 illustrates various ways in which the laser system can work together with a phacoemulsification machine and microscope setup. The figure shows a standalone phacoemulsification system 105 with a GUI screen interface 106. Integrated under the microscope 103 is the laser delivery system unit 104. This figure illustrates how (a) in a separated configuration as shown the phacoemulsification unit 105 can control the laser system and (b) furthermore the laser engine unit 101 can be integrated into the phacoemulsification unit 105 as also shown in FIG. 16.

Figure 25:
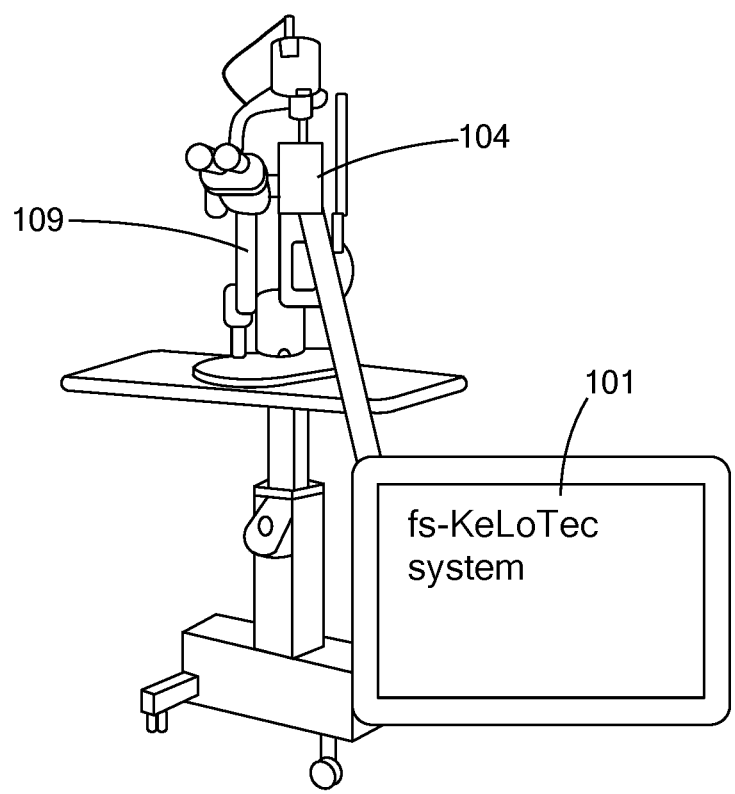
FIG. 25 illustrates the laser system integrated into a slit lamp setup.

FIG. 25 illustrates how the here described laser system can also be integrated into a slit lamp setup 109. The laser engine unit 101 and the delivery system unit 104 are illustrated.

Figure 26:
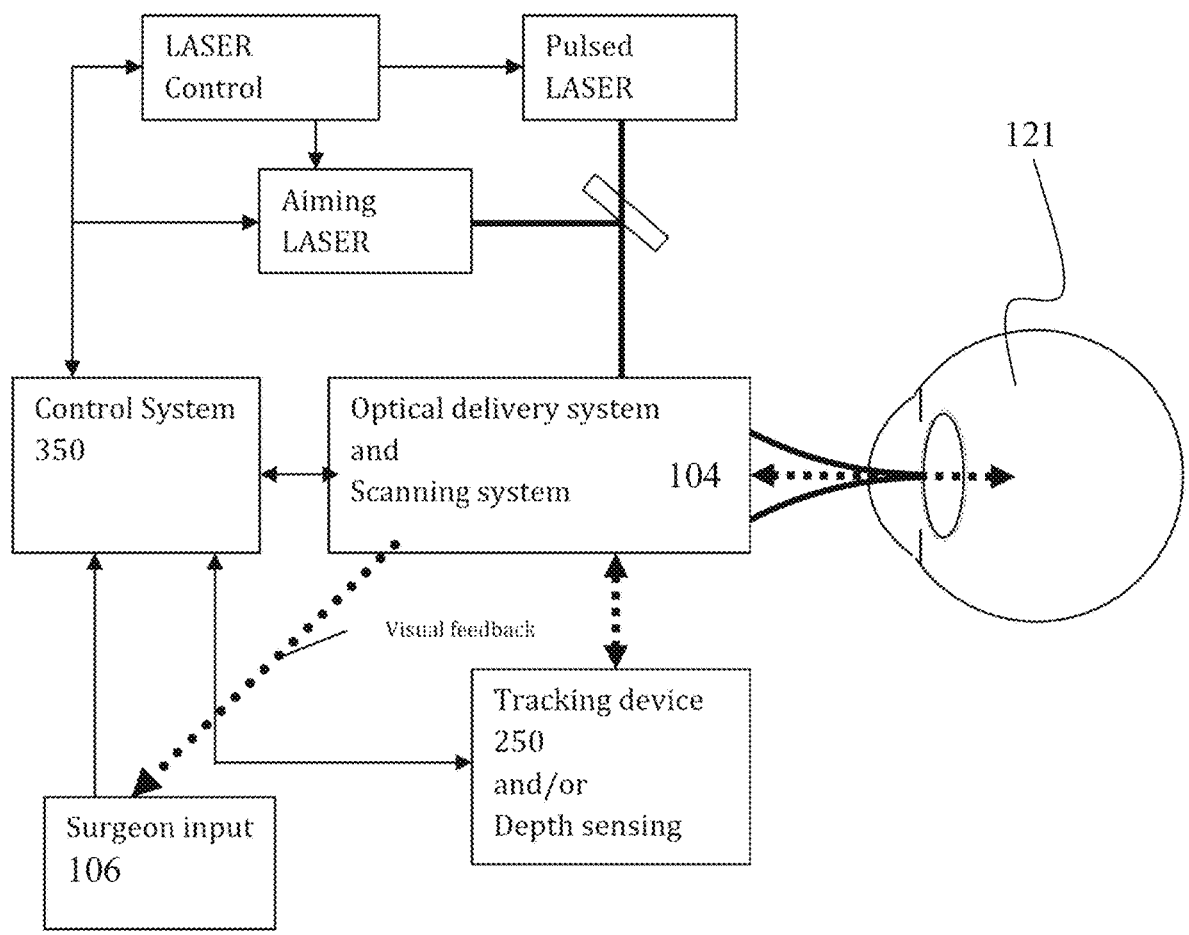
FIG. 26 shows a functional block diagram of the laser system.

FIG. 26 shows a block diagram of some laser system functionality. The surgeon receives visual feedback from the delivery system unit 104. The surgeon input interface 106 sets the control system 350 which controls the laser and the delivery system unit 104 as well as a guidance system that includes a tracking and/or depth sensing module 250 that is connected to the delivery system unit 104.

Figure 27:
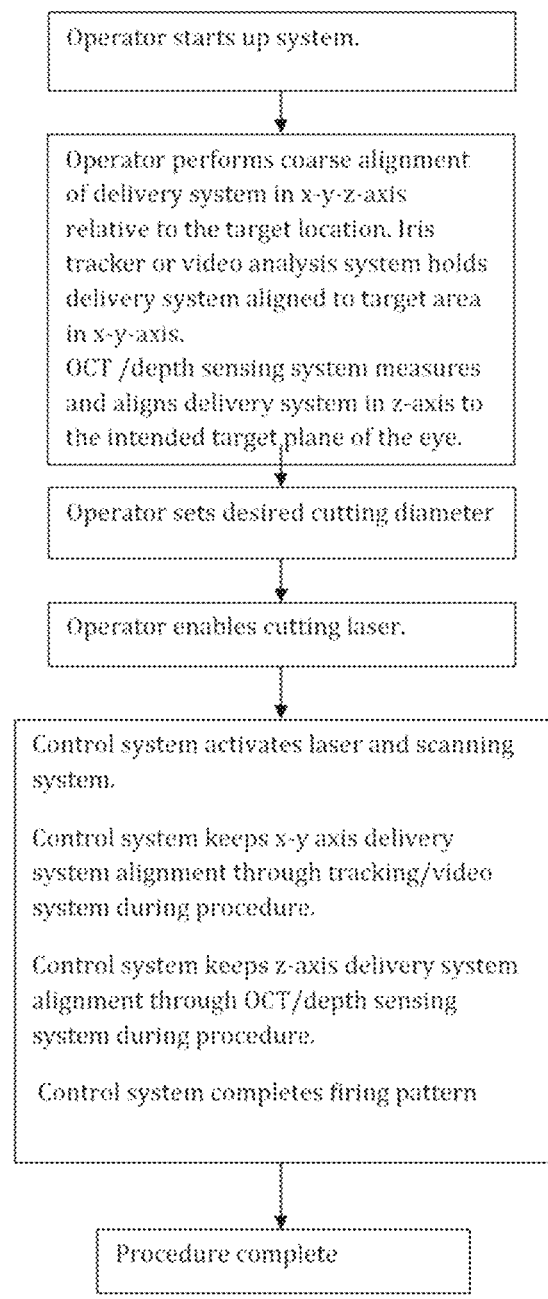
FIG. 27 shows a surgical procedure sequence.

FIG. 27 illustrates a flow diagram of a possible laser eye surgery procedure of the here described laser system which in this version includes tracking and depth sensing capabilities. After the operator starts up the system, he/she performs a coarse alignment of the delivery system in the x-y- and z axis relative to the target location. An iris tracker or a video analysis system then locks on and holds the delivery system aligned to the target area. Furthermore a Optical Coherence Tomography (OCT) or another depth sensing system measures and aligns the delivery system in the z-axis to the intended target depth plan of the eye. The operator sets a desired cutting diameter and then enables the treatment/cutting laser. The control system activates the laser and scanning system, keeps the delivery system aligned in the x-y axis through tracking during the procedure as well as in the z-axis through OCT/depth sensing during the procedure, thereby guiding the laser at all times during the procedure. The control system completes the laser firing pattern. That completes the procedure.

What is claimed is:

1. A system for eye surgery, comprising:
   a microscope system,
   a phacoemulsification system and a femtosecond laser system configured to view and cut a tissue structure of an eye with a laser beam without requiring a movement of a patient:
   the femtosecond laser system comprising a laser engine for generating a femtosecond laser beam;
   a laser delivery system defining a laser beam path;
   a swing arm;
   an articulating arm with a proximal and distal end;
   wherein the laser engine and the phacoemulsification system are contained in a housing, and wherein the articulating arm's proximal end is attached with the housing;
   wherein the femtosecond laser system is connected to the distal end of the articulating arm;
   wherein the swing arm connects the laser delivery system to the microscope;
   whereby the laser beam can be delivered to the tissue structure in the eye along the laser beam path, a phacoemulsification can be performed on the tissue structure in the eye, and the eye can be viewed through the microscope during laser beam delivery and during phacoemulsification, without moving the patient;
   wherein the swing arm is configured to be moveable between an upper and lower position relative to the microscope;

wherein when the swing arm is in the lower position, the delivery system engages the eye; and wherein the swing arm includes a precision stop that assures calibrated distances and assures alignment of the microscope and the delivery system when the swing arm is in the lower position.

* * * * *